(12) United States Patent
Tennenbaum et al.

(10) Patent No.: US 8,367,606 B2
(45) Date of Patent: Feb. 5, 2013

(54) METHOD AND COMPOSITIONS FOR PREVENTION AND TREATMENT OF DIABETIC AND AGED SKIN

(75) Inventors: Tamar Tennenbaum, Jerusalem (IL); Liora Braiman-Wiksman, Lezion (IL); Inessa Solominik, Ganei Tikva (IL); Michal Meir, Tel Aviv (IL)

(73) Assignee: HealOr Ltd., Rehovot (IL)

( * ) Notice: Subject to any disclaimer, the term of this patent is extended or adjusted under 35 U.S.C. 154(b) by 568 days.

(21) Appl. No.: 11/990,583

(22) PCT Filed: Aug. 29, 2006

(86) PCT No.: PCT/IL2006/001001
§ 371 (c)(1), (2), (4) Date: Oct. 21, 2008

(87) PCT Pub. No.: WO2007/026356
PCT Pub. Date: Mar. 8, 2007

(65) Prior Publication Data
US 2011/0021422 A1     Jan. 27, 2011

Related U.S. Application Data

(60) Provisional application No. 60/711,666, filed on Aug. 29, 2005.

(51) Int. Cl.
*C07K 14/00* (2006.01)
(52) U.S. Cl. ............................................. 514/2; 530/300
(58) Field of Classification Search .................. None
See application file for complete search history.

(56) References Cited

U.S. PATENT DOCUMENTS

| | | |
|---|---|---|
| 3,549,747 A | 12/1970 | Krezanoski et al. |
| 3,767,788 A | 10/1973 | Rankin et al. |
| 3,767,789 A | 10/1973 | Rankin et al. |
| 3,856,919 A | 12/1974 | Rankin |
| 3,907,985 A | 9/1975 | Rankin |
| 3,920,810 A | 11/1975 | Rankin |
| 3,947,573 A | 3/1976 | Rankin |
| 3,987,163 A | 10/1976 | Rankin |
| 4,029,817 A | 6/1977 | Blanco et al. |
| 4,120,949 A | 10/1978 | Bapatla et al. |
| 4,131,651 A | 12/1978 | Shah et al. |
| 4,409,205 A | 10/1983 | Shively |
| 4,558,033 A | 12/1985 | Rudman |
| 4,673,649 A | 6/1987 | Boyce et al. |
| 4,808,402 A | 2/1989 | Leibovich et al. |
| 4,833,257 A | 5/1989 | Pettit et al. |
| 4,927,636 A | 5/1990 | Hijiya et al. |
| 4,940,660 A | 7/1990 | Hirai |
| 5,019,400 A | 5/1991 | Gombotz et al. |
| 5,106,615 A | 4/1992 | Dikstein |
| 5,137,734 A | 8/1992 | Spiegelman et al. |
| 5,145,679 A | 9/1992 | Hinson |
| 5,158,935 A | 10/1992 | Nascimento et al. |
| 5,444,041 A | 8/1995 | Owen et al. |
| 5,461,030 A | 10/1995 | Lindenbaum |
| 5,591,426 A | 1/1997 | Dabrowski et al. |
| 5,591,709 A | 1/1997 | Lindenbaum |
| 5,603,943 A | 2/1997 | Yanagawa |
| 5,631,245 A * | 5/1997 | Drube .............................. 514/62 |
| 5,770,228 A | 6/1998 | Edwards et al. |
| 5,830,507 A | 11/1998 | Armstrong |
| 5,869,037 A | 2/1999 | Crystal et al. |
| 5,942,487 A | 8/1999 | Ogawa et al. |
| 5,981,606 A | 11/1999 | Martin |
| 6,028,118 A | 2/2000 | Dupont et al. |
| 6,096,288 A | 8/2000 | Roth |
| 6,174,856 B1 | 1/2001 | Langballe et al. |
| 6,274,712 B1 | 8/2001 | Springer et al. |
| 6,319,907 B1 | 11/2001 | Ferguson |
| 6,403,656 B1 | 6/2002 | River |
| 6,485,721 B1 | 11/2002 | Yoshida et al. |
| 6,489,306 B2 | 12/2002 | Mohapatra et al. |
| 6,537,973 B1 | 3/2003 | Bennett et al. |
| 6,541,447 B1 | 4/2003 | Dawson |
| 6,582,713 B2 | 6/2003 | Newell et al. |
| 6,686,334 B2 | 2/2004 | Messing et al. |
| 6,737,241 B2 | 5/2004 | Nolan et al. |
| 6,841,472 B2 | 1/2005 | Mayuzumi |
| 7,074,408 B2 | 7/2006 | Fanslow et al. |
| 7,261,881 B1 | 8/2007 | Sierra-Honigmann |
| 7,402,571 B2 | 7/2008 | Tennenbaum et al. |

(Continued)

FOREIGN PATENT DOCUMENTS

| | | |
|---|---|---|
| EP | 0 280 460 | 8/1988 |
| EP | 0 508 792 A1 | 10/1992 |

(Continued)

OTHER PUBLICATIONS

Al, et al. "The experimental study of bone marrow mesenchymal stem cells on the repair of skin wound combined with local radiation injury", *Zhonhghua Yi Xue Za Zhi*, 82(23), (2002), pp. 1632-1636; Pubmed Abstract PMID 12667374.

Alessenko, et al. "Selective changes in protein kinase C isoenzymes in rat liver nuclei during liver regeneration", *Biochem. Biophys, Commun.*, 182, (1992), pp. 1333-1339.

Andre, et al. "Protein kinases C-gamma and -delta are involved in insulin-like growth factor I-Induced migration of colonic epithelial cells", *Gastroent*.116(1) (1999), pp. 64-77.

Bajou, et al. "Absence of host plasminogen activator inhibitor 1 prevents cancer invasion and vascularization", *Nat. Med.*, 4 (1998), pp. 923-928.

Bandyopadhyay, et al. "Effects of transiently expressed atypical (ζ, λ), conventional (α, β) and novel (δ, ε) [..]", *Biochem. J.*, 337 (1999), pp. 461-470.

(Continued)

*Primary Examiner* — Anand Desai
(74) *Attorney, Agent, or Firm* — Fulbright & Jaworski LLP

(57) ABSTRACT

Method and compositions are provided for treating or preventing a skin pathology or disorder associated with diabetes and/or aging, by topical administration of at least one agent capable of restoring an impaired physiological condition of the skin associated with said skin pathology or disorder. Examples of such agents include PKC modulating agents, various adipokines and insulin signaling related molecules. In particular, restoration of the subcutaneous adipose tissue can overcome many of the diabetic skin pathologies and aging skin disorders and conditions.

12 Claims, 11 Drawing Sheets

U.S. PATENT DOCUMENTS

| | | | |
|---|---|---|---|
| 7,452,864 B2 | 11/2008 | Stahle-Baeckdahl et al. | |
| 8,012,933 B2 | 9/2011 | Stahle-Baeckdahl et al. | |
| 8,158,669 B2 | 4/2012 | Brazzel | |
| 2001/0036955 A1 | 11/2001 | Gerritsen et al. | |
| 2001/0039438 A1 | 11/2001 | Brazzel | |
| 2002/0119914 A1 | 8/2002 | Zhu et al. | |
| 2003/0017969 A1 | 1/2003 | Tennenbaum et al. | |
| 2003/0124503 A1 | 7/2003 | Olivencia-Yurvati et al. | |
| 2003/0144180 A1 | 7/2003 | Tennenbaum et al. | |
| 2003/0147855 A1 | 8/2003 | Zolotukhin et al. | |
| 2003/0148924 A1* | 8/2003 | Tennenbaum et al. | 514/3 |
| 2004/0037828 A1 | 2/2004 | Tennenbaum et al. | |
| 2004/0116499 A1 | 6/2004 | Mayser et al. | |
| 2004/0138177 A1 | 7/2004 | Park et al. | |
| 2004/0175384 A1 | 9/2004 | Mohapatra et al. | |
| 2005/0054608 A1 | 3/2005 | Linge et al. | |
| 2005/0164323 A1 | 7/2005 | Chaudhary et al. | |
| 2006/0177418 A1* | 8/2006 | Braiman-Wiksman et al. | 424/85.1 |
| 2006/0177443 A1 | 8/2006 | Fanslow et al. | |
| 2006/0258562 A1 | 11/2006 | Tennenbaum | |
| 2006/0263392 A1 | 11/2006 | Brazzel | |
| 2008/0159978 A1* | 7/2008 | Braiman-Wiksman et al. | 424/85.1 |
| 2008/0182780 A1 | 7/2008 | Linge et al. | |
| 2008/0280816 A1 | 11/2008 | Tennenbaum et al. | |
| 2008/0292726 A1 | 11/2008 | Bernstein | |
| 2008/0299654 A1 | 12/2008 | Monahan et al. | |
| 2009/0042803 A1 | 2/2009 | Terreux et al. | |
| 2010/0092452 A1 | 4/2010 | Sullivan et al. | |
| 2010/0129332 A1* | 5/2010 | Tennenbaum et al. | 424/93.21 |
| 2010/0167487 A9 | 7/2010 | Tennenbaum et al. | |
| 2010/0215634 A1 | 8/2010 | Tennenbaum et al. | |
| 2010/0310542 A1 | 12/2010 | Tennenbaum et al. | |
| 2011/0021422 A1 | 1/2011 | Tennenbaum et al. | |
| 2011/0039770 A1 | 2/2011 | Phipps et al. | |
| 2011/0223177 A1 | 9/2011 | Wormstone et al. | |
| 2011/0293707 A1 | 12/2011 | Stahle-Baeckdahl et al. | |
| 2012/0203162 A1 | 8/2012 | Brazzel | |

FOREIGN PATENT DOCUMENTS

| | | |
|---|---|---|
| EP | 0 561 330 | 9/1993 |
| EP | 0 679 402 | 2/1995 |
| GB | 2 369 572 | 6/2002 |
| JP | 63-303929 | 12/1988 |
| JP | 05-043453 | 2/1993 |
| JP | 06-510453 | 11/1994 |
| JP | 07-316066 | 12/1995 |
| JP | 08-003067 | 1/1996 |
| JP | 10-265405 | 10/1998 |
| JP | 2002-272831 | 9/2002 |
| JP | 2003-528926 A | 9/2003 |
| JP | 2006-518375 A | 8/2006 |
| RU | 2104039 | 2/1998 |
| RU | 2 115 410 C1 | 7/1998 |
| RU | 2161489 | 1/2001 |
| RU | 2 249 467 C2 | 4/2005 |
| WO | WO 85/05036 | 11/1985 |
| WO | WO 89/10129 | 11/1989 |
| WO | WO 90/11071 A1 | 10/1990 |
| WO | WO 90/11075 | 10/1990 |
| WO | WO 92/18147 | 10/1992 |
| WO | WO 93/04691 A | 3/1993 |
| WO | WO 93/25660 A1 | 12/1993 |
| WO | WO 96/09810 | 4/1996 |
| WO | WO 96/20724 | 7/1996 |
| WO | WO 96/23522 | 8/1996 |
| WO | WO 99/18920 | 4/1999 |
| WO | WO 99/34821 A1 | 7/1999 |
| WO | WO 99/35283 | 7/1999 |
| WO | WO 99/53943 | 10/1999 |
| WO | WO 00/30628 A2 | 6/2000 |
| WO | WO 01/07910 A1 | 2/2001 |
| WO | WO 01/76650 | 10/2001 |
| WO | WO 02/17980 A2 | 3/2002 |
| WO | WO 02/43751 | 6/2002 |
| WO | WO 02/009639 | 7/2002 |
| WO | WO 02/066067 A2 | 8/2002 |
| WO | WO 02/072092 A1 | 9/2002 |
| WO | WO 02/087576 A1 | 11/2002 |
| WO | WO 02/094877 A2 | 11/2002 |
| WO | WO 03/002154 A1 | 1/2003 |
| WO | WO 2005/007072 | 1/2005 |
| WO | WO 2005/009437 A1 | 2/2005 |
| WO | WO 2005/013885 A2 | 2/2005 |
| WO | WO 2005/025602 A1 | 3/2005 |
| WO | WO 2007/016777 A1 | 2/2007 |
| WO | WO 2007/026356 A2 | 3/2007 |
| WO | WO 2007/075911 A2 | 7/2007 |
| WO | WO 2009/016629 A2 | 5/2009 |
| WO | WO 2010/029350 A1 | 3/2010 |
| WO | WO 2010/007788 A9 | 9/2010 |
| WO | WO 2011/083482 A2 | 7/2011 |
| WO | WO 2011/083483 A2 | 7/2011 |

OTHER PUBLICATIONS

Benes, et al. "The C2 domain of PKC δ is a phosphotyrosine binding domain", *Cell*, 121 (2005), pp. 271-280.

Bitar, et al. "Insulin and glucocorticoid-dependent suppression of the IGF-I system I diabetic wounds", *Surgery*, 127(6) (2000), pp. 687-695.

Braiman, et al. "Tyrosine phosphorylation pf specific protein kinase C izoenzymes participates in insulin stimulation of glucose transport in primary cultures of rat skeletal muscle", *Diaetes*, 48(10) (1999), pp. 1922-1929.

Chida, et al. "The η isoform of protein kinase C is localized on rough endoplasmic reticulum", *Mol. Cell Biol*. 14 (1994), pp. 3782-3790.

Denning, et al. "Specific protein kinase C isozymes mediate the induction of keratinocyte differentiation markers by calcium", *Cell Growth Differ*., 6 (1995), pp. 149-157.

Dlugosz and Yuspa "Coordinate changes in gene expression which mark the spinous to granular call transition in epidermis are regulated by protein kinase C", *J. Cell. Biol*., 120 (1993), pp. 217-225.

Ferber, et al. "Pancreatic and duodenal homeobox gene 1 induces expression of insulin genes in liver and ameliorates [..]", *Nature Med*. 6(5) (2000) pp. 568-572.

Formisano, et al. "In NIH-3T3 fibroblasts, insulin receptor interaction with specific protein kinase C isoforms controls receptor intracellular routing", *J. Biol, Chem*., 273 (1998), pp. 12197-13202.

Frank, et al. "Leptin enhances wound re-epithelialization and constitutes a direct function of leptin in skin repair", *J. Clin. Investigation*, 2000, vol. 106, pp. 501-509.

Gcshwendt "Protein kinase Cδ", *Eur. J. Biochem*., 259 (1999), pp. 555-564.

Hengge, et al. "Epidermis as target for in vivo gene-therapy", *J. Invest. Dermatol*. 105(3) (1995) p. 448.

Hofmann "The potential for isoenzyme-selective modulation of protein kinase C", *The FASEB J*., 11 (1997), pp. 649-669.

Jeschke, et al. "IGF-I gene transfer in thermally injured rats", *Gene Ther*., 6(6) (1999), pp. 1015-1020.

Jeschke, et al. "Effect of multiple gene transfer of insulinlike growth factor I complementary DNA gene constructs in rats after thermal injury", *Arch. Surg.*, 134(10) (1999), pp. 1137-1141.

Lindenbaum, et al. "Serum-free cell culture medium induces acceleration of wound healing in guinea-pigs", *Burns*, 21(2) (1995), pp. 110-115.

MacFarlane, et al. "Glucose stimulates translocation of the homeodomain of transcription factor PDX1 from the cytoplasm to the nucleus of pancreatic bet-cells", *J. Biol. Chem.*, 274(2), (1999), pp. 1001-1016.

Madibally, et al. "Influence of insulin therapy on burn wound healing in rats", *J. Surg. Res*., 109 (2003), pp. 92-100.

Michalik, et al. "Impaired skin wound healing in perioxisome proliferator-activated receptor (PRAR) and PPAR mutant mice", *J. Cell. Biol.*, (154) (2001) pp. 799-814.

Mischak, et al. "Phorbol ester- induced myeloid differentiation is mediated by protein kinase C-α and -δ and not by protein kinase C-βII, -ε, -ζ, and -η", *J. Biol. Chem.*, 268 (1993), pp. 20110-20115.

Mischak, et al. "Overexpression of Protein Kinase C-δ and -ε in NIH 3T3 Cells Induces Opposite Effects [..]", *J. Biol. Chem.*, 268(9), (1993), pp. 6090-6096.

Mooney, et al. "Tumor necrosis factor and wound healing", *Annals of Surgery*, 211 (2), (1990) pp. 124-129.
Ohba, et al. "Induction of differentiation in normal human keratinocytes by adenovirus-mediated introduction [..] ", *Mol. Cel. Biol.*, 18(9)(1998), pp. 5199-5207.
Osada, et al. "A phorbol ester receptor/protein kinase [..]", *J. Biol. Chem.*, 265 (1990), pp. 22434-22440.
Pellegrini, et al. "Cultivation of human keratinocyte stem, cells: current and future clinical applications", *Med. Biol. Eng. Comp.* 36(6), (1998), pp. 778-790.
Perletti, et al. "Protein Kinase Cε is oncogenic in colon epithelial cell s by interaction with the *ras* signal transduction pathway", *Oncogene* 16 (1998), pp. 3345-3348.
Pittelkow, et al. "Serum-free culture of normal human melanocytes: growth kinetics and growth factor requirements", *J. Cel. Physiol.*, 140(3) (1989), pp. 565-576.
Rangwala and Lazar "Adipogenic transcriptional regulation", *Annu. Rev. Nutr.*, (20) (2000), pp. 535-559.
Reynolds, et al. "Down-regulation of langerhans cell protein kinase C-beta isoenzyme expression in inflammatory and hyperplastic dermatoses" , *Br. J. Dermatol.*, 133(2), (1995), pp. 157-167 [PMED Abstract 7547380].
Ring, et al. "Systematically and topically administered leptin both accelerate wound healing in diabetic *ob/ob* mice", *Endocrin.*, 141(1), (2000), pp. 446-449.
Servold, et al., "Growth factor impact on wound healing", *Clinics in Pod. Med. Surg.*, 8(4), (1991), pp. 937-953.
Setoguchi, et al. "Ex vivo and in vivo gene transfer to the skin using replication-deficient recombinant adenovirus vectors", *J. Invest. Dermatol.* 102(4) (1994) pp. 415-421.
Soltoff and Toker "Carbachol, substance P, and phorbol ester promote the tyrosine phosphorylation of protein kinase Cδ in salivary gland epithelial cells", *J. Biol. Chem.*, 270 (1995), pp. 13490-13495.
Spravchikov, et al., "Glucose effects on skin keratinocytes: implications for diabetes skin complications", *Diabetes*, 50(7) (2001), pp. 1627-1635.
Sun, et al. "Squamous metaplasia of normal and carcinoma in situ of HPV 16-immortalized human endocervical cells", *Cancer Res.*, 52 (1992), pp. 4254-4260.
Taran, et al. "Improved vitality of experimental random dorsal skin flaps in rats treated with enriched cell culture medium", *Plast. Reconstr. Surg.*, 104(1) (1999), pp. 148-151.
Tennenbaum, et al. "Selective changes in laminin adhesion and $\alpha_6\beta_4$ integrin regulation are associated with the initial steps in keratinocyte maturation", *Cell Growth Differ.*, 7 (1996), pp. 615-628.
Wang, et al. "Differential localization of protein kinase C δ by phorbol esters and related compounds using a fusion protein with green fluorescent protein", *J. Biol. Chem.*, 274 (1999), pp. 37233-37239.
Wertheimer, et al. "Differential roles of insulin receptor and insulin-like growth factor-1 receptor I differentiation of murine skin keratinocytes", *J. Invest. Dermatol.*, (2000), pp. 24-29.
Wertheimer, et al. "The regulation of skin proliferation and differentiation in the IR null mouse: implications for skin complications of diabetes", *Endocrin.*, 142(3) (2001), pp. 1234-1241.
Yuspa "The pathogenesis of squamous cell cancer: lessons learned from studies of carcinogenesis", *Cancer Res.*, 54 (1994), pp. 1178-1189.
Belfield, et al.: "The use of Insulin in open-wound healing", from a paper presented at 81st Annual Convention of the California Veterinary Medical Association, Oct. 3, 1969.
Greenway, et al.: "Topical insulin in wound healing: a randomised, double-blind, placebo-controlled trial", *J. Wound Care*, vol. 8, No. 10 (1999) pp. 526-528.
Kirton: Presentation at Symposium Keloids and Hypertrophic Scars, Grand Rounds, Oct. 1999; ://www.uic.edu/depts/doms/rounds/rounds-35.html.
Braiman-Wiksman, et al. "Novel Insights into Wound Healing Sequence of Events", *Toxicologic Pathology*, GB, vol. 35, No. 6, (2007), pp. 767-779.

Cataisson, et al. "Activation of Cutaneous Protein Kinase Cα Induces Keratinocyte Apoptosis and Intraepidermal Inflammation by Independent Signaling Pathways", *J. of Immunol.*, US, vol. 171, No. 5, (2003), pp. 2703-2713.
Jones, et al. "Staurosporine, a non-specific PKC inhibitor, induces keratinocyte differentiation and raises intracellular calcium, but Ro31-8220, a specific inhibitor does not", *J. of Cell. Physiol.*, vol. 159, No. 2, (1994), pp. 324-330; Abstract XP-002520100, Database EMBASE [Online], Elsevier Science Publishers, Amsterdam, NL (1994).
Liao, et al. "Effect of α-Protein Kinase C Neutralizing Antibodies and the Pseudosubstrate Peptide on Phosphorylation, Migration, and Growth of REF52 Cells", *Cell Growth and Differentiation*, vol. 4, No. 4, (1993), pp. 309-316.
Papp, et al. "Protein kinase C isozymes regulate proliferation and high cell density-mediated differentiation in HaCaT keratinocytes", *Experim. Dermatol.*, GB, vol. 12, No. 6, (2003) pp. 811-824.
Pierre, et al. "Effects of Insulin on Wound Healing", *J. of Trauma*, US, vol. 44, No. 2 (1998), pp. 342-345.
Shen, et al. "A Divergence Point in the Signaling of Insulin and IGF-1-Induced Proliferation of Skin Keratinocytes", *Diabetes*, US, vol. 50, No. 2 (2001), pp. 255-264.
Stanwell, et al. "Staurosporine induces a complete program of terminal differentiation in neoplastic mouse keratinocytes via activation of protein kinase C", *Carcinogenesis*, GB, (1996), vol. 17, No. 6, pp. 1259-1265.
Varker, et al. "Involvement of the muscarinic acetylcholine receptor in inhibition of cell migration", *Biochem. Pharmocol.*, US, vol. 63, No. 4, (2002), pp. 597-605.
Wallis, et al. "The α Isoform of Protein Kinase C Is Involved in Signaling the Response of Desmosomes to Wounding in Cultured Epithelial Cells", *Molecular Biol. of the Cell*, US, vol. 11, No. 3, (2000), pp. 1077-1092.
Yuspa, et al. "Expression of Murine Epidermal Differentiation Markers Is Tightly Regulated by Restricted Extracellular Calcium Concentrations in Vitro", *J. of Cell Biol.*, US, vol. 109, No. 3, (1989), pp. 1207-1217.
Aris, et al. "Molecular and biochemical characterization of a recombinant human PKC-delta family member", Database on NCBI.nlm.nih.gov, Genbank Accession No. L07860, Nov. 2, 1993.
Dobson, et al. "1-Butyryl-Glycerol: A Novel Angiogenesis Factor Secreted by Differentiating Adipocytes", *Cell*, 61 (1990), pp. 223-230.
Jameson, et al. "A role for skin gammadelta T cells in wound repair", *Sci.*, 296 (5568) (2002) pp. 747-749. Abstract.
Leesnitzer, et al. "Functional Consequences of Cysteine Modification in the Ligand Binding Sites of Peroxisome Proliferator Activated Receptors by GW9662", *Biochem.* 41 (2002), pp. 6640-6650.
Orgill, et al. << Design of an artificial skin. IV. Use of island graft to isolate organ regeneration from scar synthesis and other processes leading to skin wound closure.,*J. BiomedMater Res.* 39 (1998), p. 531-5, Abstract.
Smith, et al. "Peroxisomes in Dermatology. Part II", *J. Cutaneous Med. Surg.* 5(2001) pp. 315-322.
Wang, et al, "Overexpression of protein kinase C-α in the epidermis of transgenie mice results in striking alterations in phorbol ester-induced inflammation and COX-2, MIP-2 and TNF-α expression but not tumor promotion", *J. Cell Sci.* 112 (1999) pp. 3497-3506.
Reynolds, et al. "SCH 47112, a novel staurosporine derivative, inhibits 12-O-tetradecanoylphorbol-13-acetate-induced inflammation and epidermal hyperplasia in hairless mouse skin", *Arch. Dermatol. Res.*, 287 (1997). pp. 540-546.
Nishizuka: "The molecular heterogeneity of protein kinase C and its implications for cellular regulation", *Nature* vol. 334 (1988), No. 6184, pp. 661-665.
Finck et al.: "Tumor necrosis factor (TNF)-α induces leptin production through the p55 TNF receptor", *Am.J.Physiol. Regulatory Comp. Physiol.* 278 (2000), pp. R537-R543.
Cordeiro "Beyond mitomycin: TGF-β and wound healing", *Progress and Eye Res.* 21 (2002) 75-89.
Di Peppe, et al. "Adenovirus-mediated $VEGF_{165}$ gene transfer enhances wound healing by promoting angiogenesis in CD1 diabetic mice", *Gene Therapy*, (2002) 9, 1271-1277.

Volevodz, et al. "STH and IGF-I in case of diabetes mellitus: their role in pathogenesis of microvascular complications" 2000 ://www.diabet.ru/Sdiabet/2000-01/2000-01-13.htm.

Yuli "Innovative PKC modulating formulation dramatically improves the healing of diabetic wounds", *J. Investigative Dermat.* Abstract 290, XP009121582, p. A49,vol. 122, No. 3 (2004).

Traverso, et al. "Immunological evidence for increased oxidative stress in diabetic rats", *Diabetologia* (1998) 41: 265-170.

Ao, et al. "External application of insulin ointment to incurable skin ulcers", *J.Okayama Saiseikai Hen. Hosp.* 15 (1983), pp. 67-72 [English abstract only].

Kusunoki, et al. "A case of diabetic foot gangrene effectively treated by local injection of insulin" *J. of Aichi Med. Univ. Assoc.* 15 (1987), pp. 597-603 [English abstract only].

Yoshida, et al. "Topical application of insulin ointment to diabetic aging skin", IRYO 39 (1985), No. 2, pp. 147-150.

Aldhahi, et al. "Adipokines, Inflammation, and the Endothelium in Diabetes", *Current Diabetes Reports*, 3 (2003), pp. 293-298.

Badiavas, et al. "Treatment of Chronic Wounds With Bone Marrow-Derived Cells", *Arch Dermatol.*, 139 (2003), pp. 510-516.

Cordeiro "Beyond mitomycin: TGFF-62 and wound healing", *Progr. Retinal and Eye Res.* 21 (2002) pp. 75-89.

Gallucci, at al. "Interleukin-6 Treatment Augments Cutaneous Wound Healing in Immunosuppressed Mice", *J.Interf. Citokine Res.*, 21(2001) pp. 603-609.

Hussain, et al. "Identification and Characterization of Novel Lipophilic Antimicrobial Peptides Derived from Naturally Occuring Proteins", *Int'l J. Peptide Res. Ther.*, vol. 12, No. 3 (2006), pp. 269-273.

Boorsma, et al. "IP-10 mRNA expression in cultured keratinocytes is suppressed by inhibition of protein kinase-C and tyrosine kinase and elevation of cAMP", *Cytokine*, 11(7) (1999), pp. 469-475 . Abstract.

Graham, et al. "Protein Kinase C Regulation of Corneal Endothelia Cell Proliferation and Cell Cycle", *Invest. Ophtalmol. & Visual Sci.*, 41 (2000) No. 13, pp. 4124-4132.

Skvara, et al. "The PKC inhibitor AEB071 may be a threapeutic option for psoriasis", *J. Clin. Investigation*, 118 No. 9 (2008), pp. 3151-3159.

Turban, et al. "Protein kinase C isoforms: Mediators of reactive lipid metabolites in the development of insulin resistance", *J. FEBS Letters* 585 (2011), pp. 268-274.

Boorsma, et al. "IP-10 mRNA expression to cultured keratinocytes is suppressed by inhibition of protein kinase-C and tyrosine kinase and elevation of cAMP", *Cytokine*. 11(7) (1999), pp. 469-475, Abstract.

Graham, et al. "Protein Kinase C Regulation of Correal Endothelial Cell Proliferation and Cell Cycle", *Invest. Ophtalmol. & Visual Sci.*, 41 (2000) No. 13, pp. 4124-4132.

Cataisson, et al. "Protein Kinase C$\alpha$—Mediated Chemotaxis of Neutrophils Requires NF-$\kappa$B Activity but is Independent of TNF$\alpha$ Signaling in Mouse Skin In Vivo[1]", *J. Immunol.*174 (2005), pp. 1686-1692.

Denning, Mitchell "Epidermal keratinocytes: regulation of multiple cell phenotypes by multiple protein kinase C isoforms", *Int. J. Biochem. & Cell Biol.* 36 (2004), pp. 1141-1146.

Deucher, et al. "Calcium-dependent Involucrin Expression is Inversely Regulated by Protein Kinase C (PKC)$\alpha$ and PKC$\delta$", *J. Biol. Chem.* 277 No. 19 (2002), pp. 17032-17040.

Ellis, et al. "Troglitazone Improves Psoriasis and Normalizes Models of Proliferative Skin Disease", *Arch. Dermatol.* 136(5) (2000), pp. 609-616.

Ferringer, et al. "Cutaneous manifestations of diabetes mellitus", *Dermatol. Clin.* 20 (2002), pp. 483-492.

Ftich, et al. "Pathophysiology of Psoriasis: Resent Advances on IL-23 and Th17 Cytokines", *Curr. Rheumatol. Rep.* 9 (6) (2007), pp. 461-467.

Frank, et al. "Interleukin-2 Therapy in Patients with HIV Infection", *N. Engl. J. Med.*, 361 (2009), pp. 1548-1559.

Hafler, et al. "Multiple sclerosis", *Immunol. Rev.* 204 (2005), pp. 208-231.

Jansen et al. "Relation of the Induction of Epidermal Ornithine Decarboxylase and Hyperplasia to the Different Skin Tumor-Promotion Susceptibilities of Protein Kinase C$\alpha$, -$\delta$ and -$\epsilon$ Transgenic Mice", *Int. J. Cancer*, 93 (2001), pp. 635-643.

Lee, et al. "Differentiation of Cultured Human Epidermal Keratinocytes at High Cell Densities is Mediated by Endogenous Activation of the Protein Kinase C Signaling Pathway", *The Soc. for Investigative Dermatology, Inc.*(1998). pp. 762-766.

Mandil-Levin, et al., "New role for adipose tissue is skin physiology and wound healing", *J. Investig. Dermatol.* 126 (1) (2006), Abstract XP009158113.

Matsui, et al. "Protein Kinase C in Normal Human Epidermal Keratinocytes During Proliferation and Calcium-Induced Differentiation", *The Soc. for Investigative Dermatology, Inc.* (1992), pp. 565-571.

Ng, et al. "PKC$\alpha$ regulates $\beta1$ integrin-dependent cell motility through association and control of integrin traffic", *EMBRO J.* 18(14) (1999), pp. 3909-3923.

Punnonen, et al. "Keratinocycle Differentiation is Associated with Changes in the Expression and Regulation of Phospholipase C Isoenzumes", *The Soc. for Investigative Dermatology, Inc.* (1993), pp. 719-726.

Tennenbaum, et al. "The Suprabasal Expression of $\alpha6\beta4$ Integrin is Associated with a High Risk of Malignant Progression in Mouse Skin Carcinogenesis", *Cancer Res.* 53 (1993), pp. 4803-4810.

Tibudan, et al. "Activation of Protein Kinase C triggers Irreversible Cell Cycle Withdrawal I Human Keratinocytes", *The Soc. for Investigative Dermatology, Inc.* (2002), pp. 1282-1289.

Tomakidi, et al. "Discriminating expression of differentiation markers evolves in transplants of benign and malignant human skin keratinocytes through stromal interactions", *J. Pathol.*, 200 (2003), pp. 298-307.

Wang, et al. "Further identification of protein kinase C isozymes in mouse epidermis", *J. cancer Res. Clin. Oncol.*, 119 (1993) pp. 279-287 [Abstract].

Wang, et al. "Overexpression of protein kinase C$\alpha$ in the epidermis of transgenic mice results in striking alterations in phorbol ester-induced inflammation and COX-2, MIP-2 and TXF-$\alpha$ expression but not tumor promotion", *J. Cell Sci.*, 112 (1999), pp. 3497-3506.

Yang, et al. "Role of Protein Kinase C $\alpha$ in Clcium Induced Keratinocyte Differentiation: Defective Regulation in Squamous Cell Carcinoma", *J. Cell. Physiol.*, 195 (2003), pp. 249-259.

Dulbecco, et al. "Plaque formation and isolation of pure lines with poliomyelitis viruses", *J. Exp. Med.* 99(2), (1954), pp. 167-182.

Eichholtz, et al., "A Myristoylated Pseudosubstrate Peptide, a Novel Protein Kinase C Inhibitor", *J. Biol. Chem.* 268. No. 3 (1993), pp. 1982-1986.

Višnjić, et al. "Different roles of protein kinase C and isoforms in the regulation of neutral sphingomyelinase activity in HL-60 cells", *Biochem. J.* 244, (1999), pp. 921-928.

Taneja, et al. "Proinflammatory Interleukin-1 cytokines increase mesangial cell hexokinase activity and hexokinase II isoform abundance", *Am. J. Physiol.* 287 (2004), pp. C548-C557.

Zagon, et al. "Use of Topical Insulin to Normalize Corneal Epithelial Healing in Diabetes Mellitus", *Arch. Ophthalmol.* 125(8), (2007), pp. 1082-1088.

* cited by examiner

 
Fig. 3A          Fig. 3B
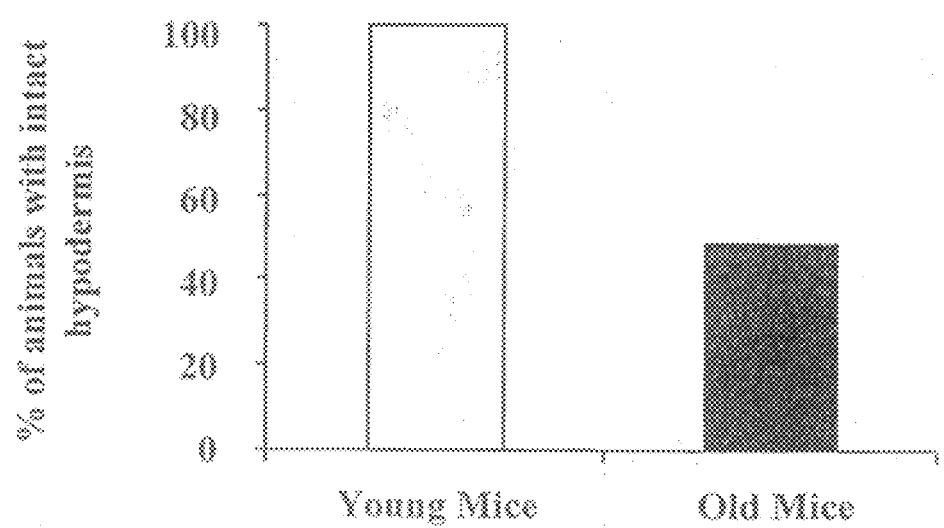
Fig. 4

SEQUENCE LISTING

<160> NUMBER OF SEQ ID NOS: 55

<210> SEQ ID NO 1
<211> LENGTH: 9
<212> TYPE: PRT
<213> ORGANISM: Artificial Sequence
<220> FEATURE:
<223> OTHER INFORMATION: The peptide is myristolated at the N terminus

<400> SEQUENCE: 1

Phe Ala Arg Lys Gly Ala Leu Arg Gln
1               5

<210> SEQ ID NO 2
<211> LENGTH: 13
<212> TYPE: PRT
<213> ORGANISM: Artificial Sequence
<220> FEATURE:

```
<223> OTHER INFORMATION: Synthetic sequence

<400> SEQUENCE: 2

Arg Phe Ala Arg Lys Gly Ala Leu Arg Gln Lys Asn Val
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Synthetic sequence

<400> SEQUENCE: 3

Arg Phe Ala Arg Lys Gly Ala Leu Arg Gln Lys Asn Val His Glu Val
1               5                   10                  15

Lys Asn

<210> SEQ ID NO 4
<211> LENGTH: 22
<212> TYPE: PRT
<213> ORGANISM: Artificial Sequence
<220> FEATURE:
<223> OTHER INFORMATION: Synthetic sequence

<400> SEQUENCE: 4

Arg Phe Ala Arg Lys Gly Ala Leu Arg Gln Lys Asn Val His Glu Val
1               5                   10                  15

Lys Asn Leu Lys Gly Ala
            20

<210> SEQ ID NO 5
<211> LENGTH: 13
<212> TYPE: PRT
<213> ORGANISM: Artificial Sequence
<220> FEATURE:
<223> OTHER INFORMATION: Synthetic sequence

<400> SEQUENCE: 5

Arg Phe Ala Arg Lys Gly Ala Leu Arg Gln Leu Ala Val
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic sequence

<400> SEQUENCE: 6

Arg Phe Ala Arg Lys Gly Ala Leu Ala Gln Lys Asn Val
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic sequence

<400> SEQUENCE: 7

Arg Phe Ala Arg Lys Gly Ala Leu Arg
1               5

<210> SEQ ID NO 8
<211> LENGTH: 13
```

```
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

Tyr Tyr Xaa Lys Arg Lys Met Ala Phe Phe Glu Phe Phe
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic sequence

<400> SEQUENCE: 9

Phe Lys Leu Lys Arg Lys Gly Ala Phe Lys Lys Phe Ala
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic sequence

<400> SEQUENCE: 10

Ala Arg Arg Lys Arg Lys Gly Ala Phe Phe Tyr Gly Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic sequence

<400> SEQUENCE: 11

Arg Arg Arg Arg Arg Lys Gly Ala Phe Arg Arg Lys Ala
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic sequence

<400> SEQUENCE: 12

Arg Phe Ala Arg Lys Gly Ala Leu Arg Gln Lys Asn Val Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic sequence

<400> SEQUENCE: 13

Asp Ala Arg Lys Gly Ala Leu Arg Gln Asn Lys Val
1               5                   10
```

```
<210> SEQ ID NO 14
<211> LENGTH: 16
<212> TYPE: PRT
<213> ORGANISM: Artificial Sequence
<220> FEATURE:
<223> OTHER INFORMATION: Synthetic sequence

<400> SEQUENCE: 14

Glu Arg Met Arg Pro Arg Lys Arg Gln Gly Ala Val Arg Arg Arg Val
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic sequence

<400> SEQUENCE: 15

Gly Pro Arg Pro Leu Phe Cys Arg Lys Gly Ala Leu Arg Gln Lys Val
1               5                   10                  15

Val

<210> SEQ ID NO 16
<211> LENGTH: 11
<212> TYPE: PRT
<213> ORGANISM: Artificial Sequence
<220> FEATURE:
<223> OTHER INFORMATION: Synthetic sequence

<400> SEQUENCE: 16

Gln Lys Arg Pro Ala Gln Arg Ser Lys Tyr Leu
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic sequence

<400> SEQUENCE: 17

Gln Lys Arg Pro Ser Gln Arg Ala Lys Tyr Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic sequence

<400> SEQUENCE: 18

Gly Gly Pro Leu Arg Arg Thr Leu Ala Val Arg Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic sequence

<400> SEQUENCE: 19

Gly Gly Pro Leu Ser Arg Arg Leu Ala Val Arg Arg
1               5                   10
```

```
<210> SEQ ID NO 20
<211> LENGTH: 12
<212> TYPE: PRT
<213> ORGANISM: Artificial Sequence
<220> FEATURE:
<223> OTHER INFORMATION: Synthetic sequence

<400> SEQUENCE: 20

Gly Gly Pro Leu Ser Arg Thr Leu Ala Val Arg Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic sequence

<400> SEQUENCE: 21

Gly Gly Pro Leu Ser Arg Arg Leu Ala Val Ala Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic sequence

<400> SEQUENCE: 22

Gly Gly Pro Leu Arg Arg Thr Leu Ala Val Ala Arg
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Synthetic sequence

<400> SEQUENCE: 23

Val Arg Lys Ala Leu Arg Arg Leu
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic sequence

<400> SEQUENCE: 24

Gly Gly Arg Leu Ser Arg Thr Leu Ala Val Ala Arg
1               5                   10

<210> SEQ ID NO 25
<211> LENGTH: 17
<212> TYPE: PRT
<213> ORGANISM: Artificial Sequence
<220> FEATURE:
<223> OTHER INFORMATION: The peptide is myristolated at the N terminus
      and amidated at the C-terminus

<400> SEQUENCE: 25

Thr Arg Lys Arg Gln Pro Ala Met Arg Arg Val His Gln Ile Asn
1               5                   10                  15

Gly
```

```
<210> SEQ ID NO 26
<211> LENGTH: 12
<212> TYPE: PRT
<213> ORGANISM: Artificial Sequence
<220> FEATURE:
<223> OTHER INFORMATION: Synthetic sequence

<400> SEQUENCE: 26

Arg Lys Arg Gln Arg Ala Met Arg Arg Arg Val His
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Synthetic sequence

<400> SEQUENCE: 27

Glu Arg Met Arg Pro Arg Lys Arg Gln Gly Ala Val Arg Arg Arg Val
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: Synthetic sequence

<400> SEQUENCE: 28

Phe Lys Leu Lys Arg Lys Gly Ala Phe Lys Lys Phe Ala
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 29

Tyr Tyr Xaa Lys Arg Lys Met Ala Phe Phe Glu Phe Phe
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic sequence

<400> SEQUENCE: 30

Ala Arg Arg Lys Arg Lys Gly Ala Phe Phe Tyr Gly Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic sequence

<400> SEQUENCE: 31

Arg Arg Arg Arg Arg Lys Gly Ala Phe Arg Arg Lys Ala
```

```
1               5                   10

<210> SEQ ID NO 32
<211> LENGTH: 20
<212> TYPE: PRT
<213> ORGANISM: Artificial Sequence
<220> FEATURE:
<223> OTHER INFORMATION: Synthetic sequence

<400> SEQUENCE: 32

Ala Ala Ala Lys Ile Gln Ala Ala Trp Arg Gly His Met Ala Arg Lys
1               5                   10                  15

Lys Ile Lys Ser
            20

<210> SEQ ID NO 33
<211> LENGTH: 19
<212> TYPE: PRT
<213> ORGANISM: Artificial Sequence
<220> FEATURE:
<223> OTHER INFORMATION: Synthetic sequence

<400> SEQUENCE: 33

Ala Ala Ala Lys Ile Gln Ala Ala Phe Arg Gly His Met Ala Arg Lys
1               5                   10                  15

Lys Ile Lys

<210> SEQ ID NO 34
<211> LENGTH: 16
<212> TYPE: PRT
<213> ORGANISM: Artificial Sequence
<220> FEATURE:
<223> OTHER INFORMATION: Synthetic sequence

<400> SEQUENCE: 34

Glu Arg Met Arg Pro Arg Lys Arg Gln Gly Ala Val Arg Arg Arg Val
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: Synthetic sequence

<400> SEQUENCE: 35

Val Arg Lys Ala Leu Arg Arg Leu
1               5

<210> SEQ ID NO 36
<211> LENGTH: 22
<212> TYPE: PRT
<213> ORGANISM: Artificial Sequence
<220> FEATURE:
<223> OTHER INFORMATION: Synthetic sequence

<400> SEQUENCE: 36

Lys Lys Lys Lys Lys Arg Phe Ser Phe Lys Lys Ala Phe Lys Leu Ser
1               5                   10                  15

Gly Phe Ser Phe Lys Lys
            20

<210> SEQ ID NO 37
<211> LENGTH: 17
<212> TYPE: PRT
<213> ORGANISM: Artificial Sequence
```

```
<220> FEATURE:
<223> OTHER INFORMATION: Synthetic sequence

<400> SEQUENCE: 37

Gly Pro Arg Pro Leu Phe Cys Arg Lys Gly Ala Leu Arg Gln Lys Val
1               5                   10                  15
Val

<210> SEQ ID NO 38
<211> LENGTH: 17
<212> TYPE: PRT
<213> ORGANISM: Artificial Sequence
<220> FEATURE:
<223> OTHER INFORMATION: Sythentic sequence

<400> SEQUENCE: 38

Glu Ser Thr Val Arg Phe Ala Arg Lys Gly Ala Leu Arg Gln Lys Asn
1               5                   10                  15
Val

<210> SEQ ID NO 39
<211> LENGTH: 16
<212> TYPE: PRT
<213> ORGANISM: Artificial Sequence
<220> FEATURE:
<223> OTHER INFORMATION: Synthetic sequence

<400> SEQUENCE: 39

Glu Arg Met Arg Pro Arg Lys Arg Gln Gly Ala Val Arg Arg Arg Val
1               5                   10                  15

<210> SEQ ID NO 40
<211> LENGTH: 13
<212> TYPE: PRT
<213> ORGANISM: Artificial Sequence
<220> FEATURE:
<223> OTHER INFORMATION: Synthetic sequence

<400> SEQUENCE: 40

Arg Phe Ala Arg Leu Gly Ala Leu Arg Gln Lys Asn Val
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 41

Tyr Tyr Xaa Lys Arg Lys Met Ala Phe Phe Glu Phe Phe
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic sequence

<400> SEQUENCE: 42

Arg Arg Phe Lys Arg Gln Gly Ala Phe Phe Tyr Phe Phe
1               5                   10
```

```
<210> SEQ ID NO 43
<211> LENGTH: 13
<212> TYPE: PRT
<213> ORGANISM: Artificial Sequence
<220> FEATURE:
<223> OTHER INFORMATION: Synthetic sequence

<400> SEQUENCE: 43

Phe Lys Leu Lys Arg Lys Gly Ala Phe Lys Lys Phe Ala
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic sequence

<400> SEQUENCE: 44

Ala Arg Arg Lys Arg Lys Gly Ser Phe Phe Tyr Gly Gly
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic sequence

<400> SEQUENCE: 45

Phe Lys Leu Lys Arg Lys Gly Ser Phe Lys Lys Phe Ala
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic sequence

<400> SEQUENCE: 46

Arg Arg Phe Lys Arg Gln Gly Ser Phe Phe Tyr Phe Phe
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 47

Tyr Tyr Xaa Lys Arg Lys Met Ser Phe Phe Glu Phe Phe
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic sequence

<400> SEQUENCE: 48
```

Arg Arg Arg Arg Arg Lys Gly Ser Phe Arg Lys Ala
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Synthetic sequence

<400> SEQUENCE: 49

Glu Arg Met Arg Pro Arg Lys Arg Gln Gly Ser Val Arg Arg Arg Val
1               5                   10                  15

<210> SEQ ID NO 50
<211> LENGTH: 12
<212> TYPE: PRT
<213> ORGANISM: Artificial Sequence
<220> FEATURE:
<223> OTHER INFORMATION: Synthetic sequence

<400> SEQUENCE: 50

Met Asn Arg Arg Gly Ser Ile Lys Gln Ala Lys Ile
1               5                   10

<210> SEQ ID NO 51
<211> LENGTH: 22
<212> TYPE: PRT
<213> ORGANISM: Artificial Sequence
<220> FEATURE:
<223> OTHER INFORMATION: Synthetic sequence

<400> SEQUENCE: 51

Met Phe Ala Val Arg Asp Arg Arg Gln Thr Val Lys Lys Gly Val Ile
1               5                   10                  15

Lys Ala Val Asp Ala Val
            20

<210> SEQ ID NO 52
<211> LENGTH: 14
<212> TYPE: PRT
<213> ORGANISM: Artificial Sequence
<220> FEATURE:
<223> OTHER INFORMATION: Synthetic sequence

<400> SEQUENCE: 52

Phe Gly Glu Ser Arg Ala Ser Thr Phe Cys Gly Thr Pro Asp
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic sequence

<400> SEQUENCE: 53

Lys Ala Arg Leu Ser Tyr Ser Asp Lys Asn
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic sequence

<400> SEQUENCE: 54

```
Ser Ala Phe Ala Gly Phe Ser Phe Val Asn Pro Lys Phe
1               5                   10

<210> SEQ ID NO 55
<211> LENGTH: 22
<212> TYPE: PRT
<213> ORGANISM: Artificial Sequence
<220> FEATURE:
<223> OTHER INFORMATION: Synthetic sequence

<400> SEQUENCE: 55

Lys Lys Lys Lys Lys Arg Phe Ser Phe Lys Lys Ser Phe Lys Leu Ser
1               5                   10                  15

Gly Phe Ser Phe Lys Lys
            20
```

METHOD AND COMPOSITIONS FOR PREVENTION AND TREATMENT OF DIABETIC AND AGED SKIN

This application is a §371 of PCT/IL/2006/001001 filed Aug. 26, 2006, and claims priority from U.S. Provisional Patent Application No. 60/711,666 filed Aug. 29, 2005.

FIELD OF THE INVENTION

The present invention relates to methods and compositions for prevention and/or treatment of skin pathologies and disorders associated with diabetes and/or aging. More particularly, the present invention relates to the use of various agents capable of restoring impaired physiological conditions of the skin associated with skin pathologies or disorders.

BACKGROUND OF THE INVENTION

Skin Physiology and Architecture

Skin is composed of a myriad of cell types, acting together to maintain overall tissue function. Normal skin physiology and architecture is dependent on the cross talk between these cells, encompassing even more intricate intracellular signaling mechanisms. The delicate balance between biochemical processes is the focus point of all physiological outcomes. This balance is the basis by which the skin exerts its physiological functions including the formation of a pathogenic barrier, modulation of the immune response, serving as an homeostatic barrier (i.e. fluid regulation), and controlling body temperature. Skin pathologies transpire when this balance is compromised and thus non desired physiological routes are expressed.

Skin is a complex tissue organized in distinct layers, namely, the epidermis, dermis and hypodermis, each possessing a different cell characterization and physiological significance (Schaefer and Redelmeier, 1996).

The epidermis is stratified squamous epithelium in which cells undergoing growth and differentiation are strictly compartmentalized (Schaefer and Redelmeier, 1996). In a normal physiologic state, proliferation is confined to the basal cells that adhere to the basement membrane. Differentiation is a spatial process in which basal cells lose their adhesion to the basement membrane, cease DNA synthesis and undergo a series of morphological and biochemical changes. The ultimate maturation step is the production of the cornified layer forming the protective barrier of the skin (Tennenbaum et al., 1991; Wysocki, 1999).

The dermis is mainly composed of matrix fibers and contains various cell types. In addition, all skin appendages, namely, microvasculature, sweat and sebaceous glands, sensory nerves and hair follicles, are localized in the dermis. The dermis has been attributed the supporting role of skin nourishment, maintaining the epidermis and the route by which signals from other parts of the body reach the outer layer (Tennenbaum et al., 1991; Wysocki, 1999).

The hypodermis is the deepest layer of the skin, mainly consisting of adipose cells, also known as the subcutaneous fat layer. Until recently, this layer has been thought to have the role of insulation from the external temperature changes and mechanical support to the upper layers of the skin (Jackson et al., 1993). Only recently, the endocrine significance of fat tissue (Pantanetti et al., 2004; Fliers et al., 2003), specifically the visceral fat tissue, has been acknowledged and identified as playing a role in glucose regulation in diabetes development and progression (Laviola et al., 2006; Maianu, 2001). Moreover, recent publications have identified the potential impact of subcutaneous adipocytes, which secrete several cytokines and growth factors that can affect skin physiology and regeneration (Nakagami et al., 2006).

Insulin Signaling in Skin

The insulin receptor is an insulin-regulated tyrosine kinase. Insulin binding to its receptor results in receptor activation via autophosphorylation of tyrosine residues on several regions of the intracellular β-subunit. Subsequently insulin receptor substrate (IRS) proteins are tyrosine phosphorylated and activated. Tyrosine-phosphorylated IRS-proteins generate downstream signals by the direct binding to the SH2 domains of various signaling proteins. Several enzymes and adaptor proteins have been identified to associate with IRS-1 and IRS-2, including phosphatidylinositol 3-kinase (PI 3-kinase), phosphotyrosine phosphatase SHP2, Grb2, Nck, and Crk. The products of the she gene are also substrates of the insulin receptor since they contain SH2 domains and are tyrosine phosphorylated in response to insulin (White, 1997).

One of the earliest steps in the insulin signaling pathway is the activation of PI 3-kinase. Once activated, the catalytic subunit phosphorylates phosphoinositides at the 3' position of the inositol ring or proteins at serine residues. PI3K activates downstream molecules such as PtdIns(3,4)P2/PtdIns(3,4,5) P3-dependent kinase 1 (PDK1), which activates serine kinase Akt. Akt in turn deactivates glycogen synthase kinase 3 (GSK-3), leading to activation of glycogen synthase and thus glycogen synthesis. Activation of Akt also results in the translocation of GLUT4 vesicles from their intracellular pool to the plasma membrane (Chang et al., 2004; Ishiki and Klip, 2005). Other targets of Akt include mTOR-mediated activation of protein synthesis by PHAS/elf4 and $p70^{s6k}$ and cell survival mechanisms represented by BAD (Bcl-2/Bcl-$X_L$ antagonist) and IKK (I-kB Kinase).

Other signal transduction proteins which interact with IRS molecules include Grb2 and SHP2. Flanking its SH2-domain, Grb2 contains two SH3-domains that associate constitutively with proline rich regions in mSOS, a guanine nucleotide exchange factor that stimulates GDP/GTP exchange on Ras. Activated Ras recruits Raf, a serine/threonine kinase to the plasma membrane. Raf activation results in the activation of MEK by phosphorylation of two serine residues. MEK is a dual specificity kinase that activates MAPK (mitogen-activated protein kinase) by both tyrosine and threonine phosphorylation. MAPK acts as an activator of some transcriptional factors (Myc, NF-kB, AP-1), kinases (Rsk), cell survival proteins (Bcl-2, cPL-2) and structural proteins (paxillin) (Taha and Klip, 1999). In addition, insulin stimulates the activation of PKC isoforms in several tissues and cell types. It has also been reported that PKC isoforms may form complexes with the IR and phosphorylate several molecules involved in IR-initiated signaling, inhibiting their function. Among serine/threonine kinases, a crucial role in modulating insulin signals is played by the PKC family members (Farese et al., 2005). For instance, PKCα has been reported to inhibit insulin action in both cellular and animal models. Overexpression of PKCα, has been shown to inhibit insulin signaling in cultured cell systems. Murine models of PKCα gene ablation also exhibit increased sensitivity to insulin, further supporting the concept of the PKCα negative role in insulin signaling by targeting insulin toward degradation. Insulin down stream signaling also involves the specific activation of PKCζ and PKCβ (Formisano et al., 2000). In addition, in skin, insulin was shown to regulate skin proliferation via PKCδ activation and transcriptional regulation of STAT3 (Gartsbein et al., 2006). Insulin also stimulates the formation of a multimolecular complex, including IRS-1 and PKCδ; PKCα inhibits IR/IRS-1 signaling and regulates insulin degradation. Insulin plays an important role in the overall regulation of protein synthesis. Some of the effects of insulin involve changes in mRNAs abundance, but insulin also has important effects on the translation process itself (Patel et al, 2006). Indeed, several initiation and elongation factors are regulated by this hormone, often as a consequence of changes in their states of phosphorylation.

Skin Pathologies in Diabetes

Skin pathologies are a common complication of diabetes, most of which are associated with progression of metabolic defects and some appear with higher incidence in diabetic patients (Wertheimer, 2004; Wertheimer and Enk, 2001). There have been reports indicating specific alteration in skin structure as well as characteristic pathologies of skin associated with the diabetic state. Diabetic patients exhibit dryer, thinner skin with a flakier outer layer; they are more exposed to skin infections caused by both bacterial and fungal sources (Wang and Margolis, 2006; Muller et al., 2005). Moreover, skin elasticity is compromised in diabetic patients similarly to skin in elderly patients, thus, having a higher tendency to break and injure (Yoon et al., 2002; Montagna and Carlisle, 1979; West, 1994). Specifically, thinned skin exhibits a reduction in rete ridges, which undermines the skins' ability to control temperature and fluid homeostasis. Furthermore, it has been demonstrated that the rete ridges serve as the enriched stem cell population of human skin. Therefore, it is clear that the rete ridges attenuation in the structure of diabetic skin results in depletion of the skin stem cell population and leads to severe impairment in skin function and remodeling (Wertheimer, 2004).

Numerous pathologies and disorders specifically associated with diabetic skin pathologies and disorders have been reported in the medical literature. These include (i) necrobiosis lipoidica diabeticorum (NLD)—appears in various stages of diabetes progression. Lesions appear circumscribed, erythematous plaques with a depressed waxy telangiectativ center characteristic of lower extremities; (ii) granuloma annulare—a chronic inflammatory disorder of unknown etiology characterized by erythematous plaques in distal extremities. Lesions are associated with advanced stages of type I diabetes; (iii) diabetic dermopathy—the most common lesion in adult diabetes, associated with the duration of the diabetic state and the appearance of other diabetic complications. Lesions appear as multiple round or oval pink to brown painless plaques; (iv) bullosis diabeticorum—bullous lesions distinctive of long term diabetes, associated with a reduced threshold to blister formation; (v) limited joint mobility—characterized by joint contractures and collagen deposition in the skin. Lesions are thought to result from changes in collagen packing, cross linking and turnover; (vi) scleredema diabeticorum—characterized by a dramatic increase in skin thickness of the posterior neck and upper back; (vii) acanthosis nigricans (AN)—lesions of dark pigmented skin which appears in body folds of the neck and axilla, associated with insulin resistance together with hyperinsulinemia; (viii) acquired perforating dermatosis—lesions characterized by transepithelial elimination of dermal components in perforating skin; (ix) insulin allergy—dermatologic side effects of continuous treatment with insulin and or hypoglycemic agents, often appears as a maculopapular rash or a pain itching erythema at injection sites; and (x) cutaneous skin infections—a common incidence in diabetic patients presenting the leading cause of morbidity and mortality (Wertheimer, 2004).

Another common denominator in these skin pathologies is the effect on the immune system of the skin, which leads to a compromise in the skins' ability to fight off external pathogens (Wang and Margolis, 2006; Muller et al., 2005). In addition, diabetic skin exhibits an impaired immune response to changes in the skin architecture brought by the metabolic complications. Such lesions result from delayed type hypersensitivity, accumulation of activated histocytes (foam cells) in the skin layers or an immune mediated response contributing to the changes in the dermis (Wertheimer, 2004). In addition, diabetic skin has been found to be constantly infected with either microbial or fungal sources due to its reduced ability to effectively react to exogenic infections. These opportunistic agents take advantage of the impaired immune response and pose a constant aggravation to patients (Wang and Margolis, 2006; Muller et al., 2005).

Skin Disorders in Aging

Skin changes are among the most visible signs of aging. Evidence of increasing age include wrinkles and sagging skin. Aging changes in the skin are a group of common conditions and developments that occur as people grow older. With aging, the outer skin layer (epidermis) thins even though the number of cell layers remains unchanged. The number of pigment-containing cells (melanocytes) decreases. Aging skin thus appears thinner, more pale, and translucent. Large pigmented spots, called age spots, liver spots or lentigos, may appear in sun-exposed areas. The subcutaneous fat layer (hypodermis), which provides insulation and padding, thins. This increases the risk of skin injury and reduces the ability to maintain body temperature. More than 90% of all older people have some type of skin disorder.

SUMMARY OF THE INVENTION

In one aspect, the present invention provides a method of treatment or prevention of a skin pathology, disorder or condition associated with diabetes and/or aging, the method comprising topically administering to the skin of a diabetic and/or aging individual a therapeutically or cosmetically effective amount of at least one agent capable of restoring an impaired physiological condition of the skin associated with said pathology, disorder or condition.

According to another aspect, the present invention provides the use of at least one agent capable of restoring an impaired physiological condition of the skin associated with a skin pathology, disorder or condition associated with diabetes and/or aging, for the preparation of a topical pharmaceutical or cosmetic composition for treatment or prevention of said skin pathology, disorder or condition in diabetic and/or aging individuals.

According to a further aspect, the present invention provides a topical pharmaceutical or cosmetic composition, when used for treating or preventing a skin pathology, disorder or condition associated with diabetes and/or aging, comprising a therapeutically or cosmetically effective amount of at least one agent capable of restoring an impaired physiological condition of the skin associated with said skin pathology, disorder or condition, optionally with a pharmaceutically or cosmetically acceptable carrier.

The methods and compositions of the invention can be used for prevention of recurrence of said skin pathology, disorder or condition in a diabetic patient.

The agents used according to the present invention include a PKC isoform modulator, an adipokine, PPARγ, a PPAR agonist or antagonist, and an agent capable of modulating the expression and/or activity of a factor involved in the insulin signaling pathway in the skin.

These agents are useful for revitalization/renewal/rejuvenation/restoration of the hypodermis/subcutaneous fat tissue/layer in diabetic and/or aging individuals and can thus be used as effective anti-aging agents.

Thus, the invention further provides a cosmetic anti-aging composition comprising a cosmetically effective amount of at least one agent capable of restoring an impaired physiological condition of the skin associated with an aging skin pathology, disorder or condition, optionally with a cosmeticaly acceptable carrier.

BRIEF DESCRIPTION OF THE FIGURES

FIGS. 3A-3B show the skin structure of normal 129 brown mouse (3A) vs. impaired insulin signaling 129 brown mice in which PKCδ deficiency was induced (3B). Skin biopsies were dissected, embedded in paraffin, and analyzed by H&E histological staining (×10 magnification Nikon Eclipse 50i microscope).

FIG. 4 shows the loss of subcutaneous fat tissue distribution in old (8 months) vs. young (8 weeks) C57BL/6J mice. Loss of subcutaneous fat tissue is presented as percent of mice with intact hypodermis layer (n=10 in each group).

DETAILED DESCRIPTION OF THE INVENTION

Figure 1A:
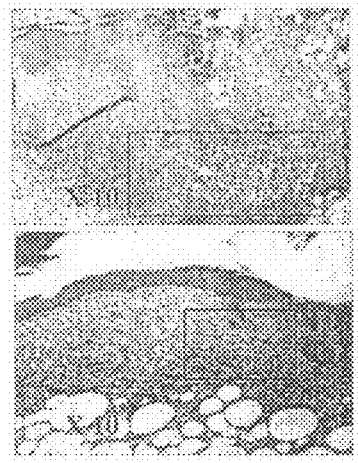
FIGS. 1A-1D show the inflammatory response in skin of diabetic (STZ injected) (1A-1B) vs. non-diabetic (1C-1D) C57BL/6J mice, demonstrating that skin of diabetic animals is prone to severe inflammatory response, indicated by facilitated abscess formation distributed among skin layers, outlined by yellow arrows. Skin biopsies were dissected, embedded in paraffin, and analyzed by H&E histological staining.
Figure 1B:
Figure 1C:
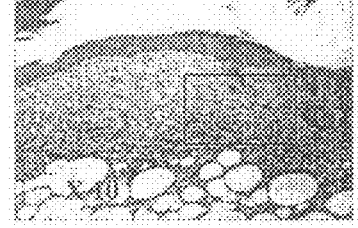
Figure 1D:
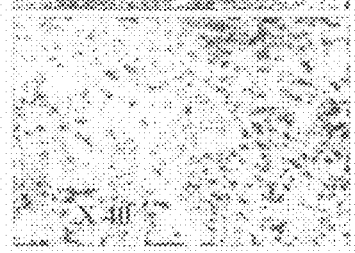

The present invention relates to methods, pharmaceutical and cosmetical compositions for treatment and/or prevention of skin pathologies, disorders and conditions associated with the diabetic and/or aging skin.

The principles and operation of the methods and compositions according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or exemplified in the Examples section. The invention is capable of other embodiments or of being practiced or carried out in various ways. Also, it is to be understood that the phraseology and terminology employed herein is for the purpose of description and should not be regarded as limiting.

As used herein, the terms "skin pathology" and "skin disorder" do not include wounds and, in particular, do not include the types of wounds defined in the previous patent applications U.S. Ser. No. 09/629,970, U.S. Ser. No. 10/169,801, U.S. Ser. No. 11/332,774, U.S. Ser. No. 11/348,527, WO 02/09639, WO 2005/007072 and WO/2005/013885. Specifically, the terms "skin pathology" and "skin disorder" do not include an ulcer, a diabetes-related wound, a burn, a sun burn, an aging skin wound, a corneal ulceration wound, an inflammatory gastrointestinal tract disease wound, a bowel inflammatory disease wound, a Crohn's disease wound, an ulcerative colitis, a hemorrhoid, an epidermolysis bulosa wound, a skin blistering wound, a psoriasis wound, an animal skin wound, a proud flesh wound, an animal diabetic wound, a retinopathy wound, an oral wound (mucositis), a vaginal mucositis wound, a gum disease wound, a laceration, a surgical incision wound and a post surgical adhesions wound As used herein, the terms "diabetic skin" and "skin pathology, disorder or condition associated with diabetes" are used interchangeably to define a skin disorder that is caused by diabetes or is affected by diabetes. Some of these disorders are conditions that anyone can have but to which people with diabetes are particularly prone, such as atherosclerotic skin changes, bacterial and fungal infections of the skin, and itching. Other diabetic skin diseases are seen mainly or exclusively in people with diabetes and include those pathologies summarized in Table 1, in which the compartmentalization of the different pathologies to affected cells/tissues, enables better understanding of the disorders and treatment of the common impairments associated with diabetic skin.

TABLE 1

Skin pathologies related to diabetes and cell/tissue associated therewith

| Pathology | Cells/tissue associated with | Clinical and histological manifestation |
| --- | --- | --- |
| NLD | matrix/dermis | Thickening of collagen |
| Granuloma annulare | matrix/dermis | Focal degeneration of collagen |
| Diabetic dermopathy | matrix/dermis | Atrophic dermis with fibroblast proliferation, fibrotic collagen |
| Scleroderma diabeticorum | matrix/dermis/fat | Enlarged dermis through the replacement of subcutaneous fat by collagen fibers |
| APD | matrix/dermis | Transversing collagen/elastin to epidermis |
| Bullosis diabeticorum | epidermis | Reduced threshold to blister formation |
| Acanthosis nigricans | epidermis | Thick epidermis and altered dermal papills |
| APD | epidermis | Primary epidermal defect, thick epidermis |
| Cutaneous infections | epidermis | Breach in pathogenic barrier, reduction in immune cells in the epidermis |

By focusing on the cells and biochemical changes in the different skin cells we are able to further compartmentalize the diabetes-related skin complications. Specifically, epidermal-related defects can be associated either to impaired proliferation/differentiation ratio or breach of cell-cell or cell-matrix (basement membrane) contact (Wertheimer et al., 2001; Alt et al., 2001). Dermal/matrix-related defects may be influenced by the differentiation capacity of fibroblast inhabiting the dermal layer. Fibroblasts, the most common cell type in the dermis, are known to be responsible for the collagen and elastin fiber network synthesis and maintenance. In the dermis, fibroblasts are found in all differentiation stages from stem cells through intermediate stages and the fully differentiated committed fibroblast. It is the mature cell that is responsible for matrix formation (Freinkel and Woodley, 2001); thus, any disturbance in fibroblast differentiation may contribute to matrix imperfections. In addition, fibroblast depletion by reduced proliferation might also contribute to impaired matrix formation and/or maintenance.

Concomitantly, adipose cell in the hypodermis are also dependent on their dedifferentiation state in order to exert their endocrine role in skin physiology (Gregoire, 2001).

The inventors of the present invention have developed a reliable technique for quantitatively identifying the critical parameters in skin physiology. These parameters are specifically linked to signaling pathways leading to physiological processes including proliferation, migration, differentiation, matrix formation and maintenance. Establishing the link between the parameters is of great importance in primary prevention and treatment of skin complications of diabetic patients. Thus, by underlying the biochemical regulation of these processes, we are able to control specific signaling pathways leading to the desired physiological endpoints. It is important to take into consideration that many of these pathways interact and influence each other, implying that only a combined regulation will be able to effectively direct the desired outcome.

From our observations it is clear that the epidermis of diabetic skin exhibits a disrupted basal layer where the cells appear with large nuclei and are not set vertically as in normal skin. It can be also observed that the elastin in the dermis disappears from under the epidermis and disintegration is characteristic of fibers in the deeper part of the dermis. Concurrently, there have been reports that diabetic skin exhibits a reduction in fibroblast number which is the rationale for the reduction in procollagen and thus reduced collagen content (Varani et al., 2006). Advanced glycation endproduct formation, caused by the consistent hyperglycemia, have been thought to affect directly various skin structures such as the microvasculature, dermal collagen fibers and basement membrane (Yang et al., 2003). Hyperglycemia has also been shown to have a direct effect on the epidermal keratinocytes, modifying their ability to proliferate and differentiate (Spravchikov et al., 2000).

Our results in accordance with the present invention further imply a crucial role for subcutaneous adipocytes in diabetes complications in skin. Progression of diabetes and deterioration of skin elasticity and strength is directly linked to the disregulation of adipocytes differentiation and distribution leading to the loss of the hypodermis tissue/subcutaneous fat layer. In addition, the diabetic state affects the immune response of skin thus preventing its proper function in guarding the skin from pathogens and stress-related disorders (Tingo et al., 2006). Taken together, it is clear that the diabetic metabolic syndrome directly affects skin through various routes and involves almost every skin-related cell.

While diabetic skin is unique in its characteristics, some of the diabetic associated pathologies resemble defects characteristic of the aging state. Therefore, a similar approach can be directed to revitalizing aging skin to induce skin rejuvenation.

Thus the defects found in diabetic patients in general, including aged diabetic patients, and in non-diabetic aging individuals, can be corrected in accordance with the present invention specifically by renewal of the various cell layers of skin, particularly the hypodermis layer. This is a novel approach to correct esthetic defects, restore elasticity and rejuvenate skin in diabetic and non-diabetic individuals and to prevent appearance or recurrence of a pathology associated with diabetic skin.

In one aspect, the present invention provides a method for treating or preventing a skin pathology, disorder or condition associated with diabetes and/or aging, comprising topically administering to the skin of a diabetic and/or aging individual a therapeutically or cosmetically effective amount of at least one agent capable of restoring an impaired physiological condition of the skin associated with said skin pathology, disorder or condition.

As used herein, the term "impaired physiological condition of the skin associated with said skin pathology or disorder", when related to the diabetic skin, refers to all pathologies that impair biochemical balance and structure of the skin, such as disappearance of the hypodermis adipose layer; impaired integrity of the epidermis layer through the disrupted regulation of the differentiation process and proliferation capacity, which is frequent in diabetic skin; dermis exhibition of disseminated matrix deposition affecting collagen distribution, elastic fibers destruction and enhanced inflammatory response throughout all skin layers, which are characteristic of diabetic skin. As a result of these changes of the physiological conditions, distinct skin pathologies specific to the diabetic state are induced, as specified herein in the specification. In addition, these impairments induce also general changes such as thinning, dryness, abundance of skin tags and loss of general esthetics. As far as aged skin is concerned, in addition to changes in matrix deposition and dermis structures, which are known, the term also refers to a unique impairment in the hypodermis layer, which we have characterized in the present invention, which leads to the impairment of aging skin including impaired elasticity, thinning, wrinkles, etc. The term also refers to the biochemical impairments in the insulin signaling pathway, PKC pathways and adipokine secretion in diabetic and aged skin that specifically cause structural pathological manifestations including changes in epidermis, dermis and uniquely in the hypodermis. As we recognized the main molecules and their role in these skin problems, we show herein several possible pathway-related treatments which overcome the impairments associated with diabetic and aging skin.

The in vitro and in vivo models developed and described in Material and Methods section hereinafter, allow quantification of stage-specific changes in the normal and diabetic skin. Our models provide the utilization of morphological, histological and immunohistochemical analysis for the identification of target specific modulators facilitating the formulation of efficient treatments.

In one embodiment of the present invention, the at least one agent is a PKC isoform modulator capable of modulating the expression and/or activity of at least one PKC isoform.

The term "PKC isoform" as used herein encompasses all PKC isoforms including PKCα, PKCβ (including both PKCβ1 and PKCβ2), PKC-δ, PKC-ε, PKC-η, PKC-ζ, PKC-γ, PKC-θ, PKC-λ and PKC-τ. In preferred embodiments, the PKC isoform is PKCα, PKCδ, PKCε or PKCζ.

The phrase "modulating expression and/or activity of a PKC isoform" relates to an increased or reduced expression and/or activity of a PKC isoform. Increase of the expression leads to increased production of the PKC isoform. The term "PKC activator" is used herein interchangeably with the term "PKC isoform activator" to describe a molecule that enhances expression and/or activity of a PKC isoform.

The term "PKC inhibitor" is used herein interchangeably with the term "PKC isoform inhibitor" to describe a molecule that inhibits expression and/or activity of a PKC isoform.

Among others, the phosphoryl transfer region, the pseudosubstrate domain, the phorbolester binding sequences, and the phosphorylation sites may be targets for modulation of isoenzyme-specific PKC activity (Hofmann, 1997). It should be understood that many modulators are not specific and sometimes the modulator may be both inhibitor and activator.

In one embodiment, the at least one agent is a PKC isoform inhibitor, which may be a PKC isoform pseudosubstrate inhibitor, a peptide binding to the PKC isoform substrate region, a peptide binding to the ATP-binding site of a PKC isoform, or Copolymer-1.

The "pseudosubstrate region" or autoinhibitory domain of a PKC isoform is defined as a consensus sequence of substrates for the kinase with no phosphorylatable residue. The pseudosubstrate domain is based in the regulatory region, closely resembling the substrate recognition motif, which blocks the recognition site and prevents phosphorylation. Thus, inhibitory peptides are obtained by replacing a phosphorylatable residue of serine (S) or tyrosine (T) by alanine (A). PKCδ is the only PKC isoform known to have additional binding site enabling the isoform's activation on the C2 domain, the conserved domain 2 of PKCδ (Benes et al., 2005).

The ATP-binding sites of all PKC isoforms are known from the literature. Any peptide that binds to the ATP-binding site will inhibit the activity of the PKC isoform.

The PKC isoform inhibitor is preferably a PKCα, PKCβ, PKCη or PKCζ inhibitor, more preferably a PKCα or a PKCη inhibitor.

Examples of PKCα inhibitors that can be used according to the present invention include, without being limited to, a PKCα pseudosubstrate inhibitor such as the peptides of SEQ IDS NO: 1-7, and a peptide binding to the substrate region such as the peptides of SEQ ID NO: 8 to NO. 24. The peptides of SEQ ID NO: 1 to NO: 24 may be N-acylated, preferably by an acyl group derived from a C12-C20 fatty acid, more preferably $C_{14}$-acyl (myristoyl). In one most preferred embodiment, the PKCα inhibitor is the N-myristoylated PKC-α pseudosubstrate peptide of SEQ ID NO: 1. It may be administered in a therapeutically or cosmetically effective concentration ranging from 0.01 μM to 10 μM, preferably 0.1-5 μM, 0.5-2 μM, or 1-2 μM, more preferably 1 μM for therapeutic purposes, and at a lower concentration for cosmetic purposes, more preferably 0.1 μM.

Examples of PKCη inhibitors that can be used according to the present invention include, without being limited to, a PKCη pseudosubstrate inhibitor such as the N-myristoylated peptide of SEQ ID NO: 25, a PKCη inhibitor that binds to the substrate region such as the peptides of SEQ ID NO: 26 and NO: 27, and Copolymer 1 (the active ingredient of the drug glatiramer acetate/Copaxone®, of Teva Pharmaceutical Industries Ltd., Petach Tikva, Israel), clinically used for treating multiple sclerosis. Copolymer-1 is a synthetic polypeptide analog of myelin basic protein (MBP), which is a natural component of the myelin sheath. Chemically, Copolymer-1 is a random copolymer of the 4 amino acids L-glutamic acid, L-alanine, L-lysine and L-tyrosine. In the form of its acetate salt it is known as glatiramer acetate and has an average molecular weight of 4,700-11,000 daltons. Copolymer-1 molecules of higher molecular weight are also known (MW 15,000-18,000) and can be used according to the present invention. As disclosed in U.S. patent application Ser. No. 11/332,774, herewith incorporated by reference in its entirety as if fully described herein, Copolymer-1 was discovered to be a specific and very effective PKCη inhibitor.

Examples of PKCβ inhibitors that can be used according to the present invention include, without being limited to, a PKCβ inhibitor that binds to the substrate region such as the peptides of SEQ ID NO: 28 to NO: 38.

Examples of PKCζ inhibitors that can be used according to the present invention include, without being limited to, a PKCζ inhibitor that binds to the substrate region such as the peptides of SEQ ID NO: 39 to NO: 43.

According to another embodiment, said PKC isoform modulator used in the methods and compositions of the present invention is a PKC isoform activator, preferably a PKCδ, PKCε or PKCζ activator, more preferably a PKCδ activator.

The PKC isoform activator may be, without being limited to, a peptide binding to a PKC isoform substrate region, a peptide acting on a PKC isoform phosphorylation site, insulin, bryostatin, a PKC isoform RACK peptide or a MARCKS (myristoylated alanine-rich C kinase substrate)-derived peptide.

Examples of PKCδ activators that can be used according to the present invention include, without being limited to, insulin, a peptide binding to the PKCδ substrate region such as those of SEQ ID NO: 44 to NO: 51; a peptide acting on the PKCδ phosphorylation site such as those of SEQ ID NO: 52 to NO: 54; a PKCδ RACK peptide, and peptides corresponding to the C2 domain (disclosed in Benes et al., 2005). In a more preferred embodiment, the PKCδ activator is insulin, administered in a pharmaceutical or cosmetic composition in a concentration ranging from 0.01 μM to 10 μM, preferably 0.01-2 μM, more preferably $7 \times 10^{-7}$ M (0.1 unit) for therapeutic purpose and $7 \times 10^{-8}$ M (0.01 unit) for cosmetic purpose.

Examples of PKCε activators that can be used according to the present invention include, without being limited to, a PKCε RACK peptide. Examples of PKCζ activators that can be used according to the present invention include, without being limited to, the PKC-ζ MARCKS-derived peptide of SEQ ID NO: 55.

In one embodiment, more than one agent, preferably two or three different PKC isoforms modulators, can be used in the methods/compositions of the present invention.

In one preferred embodiment, two agents are used and the agents may be: (i) a PKCα inhibitor, preferably the N-myristoylated peptide of SEQ ID NO: 1, and a PKCδ activator, preferably insulin; (ii) a PKCη inhibitor, preferably Copolymer-1 or the N-myristoylated peptide of SEQ ID NO: 25, and a PKCδ activator, preferably insulin; and (iii) a PKCα inhibitor, preferably the N-myristoylated peptide of SEQ ID NO: 1, and a PKCη inhibitor, preferably Copolymer-1 or the N-myristoylated peptide of SEQ ID NO: 25. The concentrations of the peptide of SEQ ID NO:1 and of insulin are as defined above for therapeutic and cosmetic purposes. The concentration of Copolymer 1 is in the range of 0.5-60 μg/ml, preferably 10-55 μg/ml or 50-55 μg/ml, more preferably about 55 μg/ml.

In a further preferred embodiment, three agents are used, for instance, a PKCα inhibitor, preferably the N-myristoylated peptide of SEQ ID NO: 1, a PKCη inhibitor, preferably Copolymer-1, and a PKCδ activator, preferably insulin.

The insulin for use in the methods and compositions of the present invention may be recombinant or from a natural source such as human insulin or a non-human mammal insulin that is suitable for human use such as porcine insulin.

In another embodiment of the present invention, the at least one agent is an adipokine, a bioactive molecule secreted by adipocytes selected from adipocyte-secreted enzymes, growth factors, cytokines and hormones. Examples of adipokines include, but are not limited to, complement factors D (adipsin), C3 and B, adiponectin (Acrp30), apelin, visfatin, resistin, leptin, lipoprotein lipase (LPL), plasminogen activator inhibitor-1 (PAI-1), tumor necrosis factor-α (TNF-α), interleukin-1β (IL-1β), IL-4, IL-6, IL-8, angiotensin I-IV (angiotensin IV is an active angiotensin II fragment) and cycloanalogues thereof, angiotensinogen, 1-butyrylglycerol (monobutyrin), matrix metalloproteinase 2, matrix metalloproteinase 9, acylation stimulating protein (ASP), vaspin, omentin, and neuropeptide Y.

In one preferred embodiment, the adipokine is adiponectin that can be used in a concentration of 0.01-1 μg/ml, preferably 0.1 μg/ml.

In a further embodiment, the at least one agent is PPARγ (peroxisome proliferators-activated receptor-γ), a transcription factor expressed in adipocytes, keratinocytes and sebaceous glands, or it is a PPAR agonist or antagonist. In one embodiment, the agent is a PPARγ antagonist such as GW9662 (2-chloro-5-nitrobenzanilide) or a PPARγ agonist such as a thiazolidinedione derivative, e.g., troglitazone [5-(4-(6-hydroxy-2,5,7,8-tetramethylchroman-2-yl-methoxy) benzyl)-2,4-thiazolidinedione)], rosiglitazone [5-(4-(2-(methyl-2-pyridinylamino)ethoxy)phenyl)methyl)-2,4-thiazolidinedione), or the partial PPARγ agonist GW0072, a potent antagonist of adipocyte differentiation. In other embodiments, the agent is a PPARα agonist such as GW7647 and BM-17.0744, a PPARδ agonist such as GW0742, or a PPAR non-subtype selective agonist such as GW2433, GW4148, GW2331 and L165041.

In one preferred embodiment, the PPARγ agonist is troglitazone or rosiglitazone that can be used in a concentration of 2-300 nM, preferably 10-200 nM, 20-150 nM, 20-100 nM, or 20-50 nM, preferably 50 nM or 20 nM for cosmetic purposes. In another embodiment, the agent is a PPAR antagonist that can be used in a concentration of 1-100 nM.

In a further embodiment, the at least one agent is capable of modulating the expression and/or activity of a factor involved in the insulin signaling pathway in the skin.

In one embodiment, the agent directly activates the expression and/or activity of the insulin receptor (IR). Examples of IR activators that can be used according to the present invention include, without being limited to, TLK16998; TLK19781; 2,5-dihydroxy-3-(4-methoxyphenyl)-6-phenyl-2,5-cyclohexadiene-1,4-dione, 2,5-dihydroxy-3-(1-methyl-1H-indol-3-yl)-6-phenyl-2,5-cyclohexadiene-1,4-dione, and 1,2,3,4,6-penta-O-galloyl-D-glucopyranose.

In another embodiment, the agent acts downstream to the IR modulating specific target pathways downstream to the IR. Examples of such agents include, without being limited to, a phosphatidylinositol 3-kinase (PI3K) modulator, a protein kinase B/Akt modulator, a glycogen synthase kinase-3 (GSK3) modulator, a Raf modulator, a renin-angiotensin system (Ras) modulator, a mitogen-activated protein kinase (MAPK) modulator, an ERK modulator, a JNK modulator, or a MEK modulator.

Examples of such modulators include, but are not limited to, a PI3K inhibitor such as PTEN, Wortmannin and LY 294002; an Akt inhibitor such as NL-71-101 or an Akt activator such as the mammalian target of rapamycin (mTOR); a GSK3 inhibitor such as the compounds CT 20026, CHIR 98014 and CHIR 99021; a Raf inhibitor such as BAY 43-9006 (sorafenib); a p38-MAPK inhibitor such as SB203580; a ERK inhibitor such as PD09859; a JNK inhibitor such as SP600125; and a MEK inhibitor such as PD98059 or UO126.

Any skin pathology or disorder associated with diabetes can be treated and/or prevented by the method of the present invention including, but not limited to, skin thinning, epidermal thinning, skin dryness, abnormal differentiation pattern in epidermis, reduction in proliferation in all skin layers, absence/irregularity of the hypodermis subcutaneous adipose tissue, fragility, reduced skin tone, loss of skin moisture, sagging of skin; skin hyperpigmentation and discoloration, irritated and sensitive skin; increased inflammation in skin, loss of skin texture, disruption of matrix fiber (collagen and elastin) structure, loss of skin smoothness and firmness, loss of elasticity, limited oil/sebum secretion, necrobiosis lipoidica diabeticorum (NLD), granuloma annulare, diabetic dermopathy, bullosis diabeticorum, limited joint mobility, scleredema diabeticorum, acanthosis nigricans, acquired perforating dermatosis, insulin allergy, cutaneous skin infections, or xanthoma (benign lesions of lipid-laden foam cells-yellow lesions). Also included are skin disorders due to disturbance of carbohydrate metabolism such as itching, pyoderma, candidosis, eczema, porphyria cutanea tarda (PCT), and panniculitis.

In addition, treatment of all skin disorders or conditions associated with aging as described below is applicable for diabetic aging individuals.

In one embodiment, the method of the invention is applied when the skin pathology or disorder is associated with diabetes and said at least one agent is administered in a pharmaceutical composition comprising a therapeutically effective amount of said at least one agent. In one preferred embodiment, the pharmaceutical composition comprises a pharmaceutically acceptable carrier and the N-myristoylated PKCα pseudosubstrate peptide of SEQ ID NO: 1 in a concentration ranging from 0.01 μg/ml to 10 μg/ml, preferably 0.1-5 μg/ml, 0.5-2 μg/ml, or 1-2 μg/ml, more preferably 1 μg/ml, optionally in combination with insulin in a concentration ranging from 0.01 μg/ml to 10 μg/ml, preferably 0.1-2 μg/ml, more preferably 0.1 μg/ml.

In another embodiment, the method of the invention is applied when the skin pathology, disorder or condition is associated with diabetes and said at least one agent is administered in a cosmetic composition comprising a cosmetically effective amount of said at least one agent. In one preferred embodiment, the pharmaceutical composition comprises a cosmetically acceptable carrier and the N-myristoylated PKCα pseudosubstrate peptide of SEQ ID NO: 1 in a concentration ranging from 0.01 μg/ml to 10 μg/ml, preferably 0.1-5 μg/ml, 0.5-2 μg/ml, or 1-2 μg/ml more preferably 0.1 μg/ml, optionally in combination with insulin in a concentration ranging from 0.01 μg/ml to 10 μg/ml, preferably 0.1-2 μg/ml, more preferably 0.1 μg/ml.

In another embodiment, the method of the invention is applied when the skin disorder or condition is associated with aging and said at least one agent is administered in a cosmetic composition comprising a cosmetically effective amount of said at least one agent. In one preferred embodiment, the pharmaceutical composition comprises a cosmetically acceptable carrier and the N-myristoylated PKCα pseudosubstrate peptide of SEQ ID NO: 1 in a concentration ranging from 0.01 μg/ml to 10 μg/ml, preferably 0.1-5 μg/ml, 0.5-2 μg/ml, or 1-2 μg/ml, more preferably 0.1 optionally in combination with insulin in a concentration ranging from 0.01 μg/ml to 10 μg/ml, preferably 0.1-2 μg/ml, more preferably 0.1 μg/ml.

The disorders or conditions associated with aging that can be treated by the method of the invention include, but are not limited to, dry and flaky skin, skin thinning, flattening of rete ridges, actinic elastosis, wrinkles, crow's feet, liver spots, age spots, skin hyerpigmentation, discoloration, facilitated blistering, fragility, reduced skin tone, reduced threshhold for irritation, loss of tautness and sagging, loss of elasticity, laxity, hyperplastic and disorganized elastic fiber system, reduced skin flexibility, reduced acral and sweat glands, reduced sebum production, trans epidermal water loss (TEWL) resulting in loss of moisture.

The invention also provides a method for prevention of recurrence of a skin pathology or disorder in a diabetic patient, comprising topically administering to the skin of said diabetic patient a therapeutically or cosmetically effective amount of at least one agent as defined above capable of restoring an impaired physiological condition of the skin associated with said skin pathology or disorder.

The invention further relates to a method for revitalization/rejuvenation/renewal of the subcutaneous fat layer of a diabetic or aging individual, which comprises topically administering to the skin of said individual a cosmetically effective amount of at least one agent as defined above capable of causing renewal of the hypodermis layer.

The invention still further relates to the use of at least one agent capable of restoring an impaired physiological condition of the skin associated with a skin pathology, disorder or condition associated with diabetes and/or aging, for the preparation of a topical pharmaceutical or cosmetic composition for treatment or prevention of said skin pathology or disorder in diabetic and/or aging individuals.

Also provided by the invention are pharmaceutical and cosmetic compositions for topical application for treatment or prevention of skin pathologies, disorders or conditions in diabetic and/or aging individuals comprising a pharmaceutically or cosmetically acceptable carrier and at least one agent as defined above capable of restoring an impaired physiological condition of the skin associated with said skin pathology, disorder or condition associated with diabetes and/or aging.

The therapeutically/pharmaceutically/cosmetically active ingredients used in the present invention can be administered to the diabetic or aging skin per se, or in a pharmaceutical or cosmetic composition mixed with suitable carriers and/or excipients. Pharmaceutical compositions suitable for use in context of the present invention include those compositions in which the active ingredients are contained in an amount effective to achieve an intended therapeutic effect. Cosmetic compositions suitable for use in context of the present invention include those compositions in which the active ingredients are contained in an amount effective to achieve an intended cosmetic effect.

The pharmaceutical and cosmetic compositions of the invention are intended for topical application and may be in the form of an aqueous solution, a gel, a cream, a paste, a lotion, a spray, a suspension, a powder, a dispersion, a salve, an ointment, a serum, an anhydrous stick, oil based sprays, oil-in-water emulsions or water-in-oil emulsions.

The term "topical application" as used herein refers to external application to the skin, mucous membranes, teeth, hair, scalp.

As used herein, the terms a "pharmaceutical composition" and a "cosmetic composition" refer to a preparation of one or more of the active ingredients described herein, or physiologically acceptable salts or prodrugs thereof, with other chemical components such as traditional drugs, physiologically suitable carriers and excipients suitable for therapeutic or cosmetic use. The compositions of the present invention may be manufactured by processes well known in the art, e.g., by means of conventional mixing, dissolving, granulating, dragee-making, levigating, emulsifying, encapsulating, entrapping or lyophilizing processes.

Hereinafter, the phrases "pharmaceutically suitable carrier" and "cosmetically or dermatologically acceptable carrier" refer to a carrier or a diluent that does not cause significant irritation to an organism and does not abrogate the biological activity and properties of the administered ingredients. In the pharmaceutical compositions, inert substances are added to further facilitate processes and administration of the active ingredients and these excipients include, without limitation, calcium carbonate, calcium phosphate, various sugars and types of starch, cellulose derivatives, gelatin, vegetable oils and polyethylene glycols. Techniques for formulation and administration of active ingredients may be found in "Remington's Pharmaceutical Sciences," Mack Publishing Co., Easton, Pa., latest edition, which is incorporated herein by reference.

While various routes for the administration of active ingredients are possible, for the purpose of the present invention, the topical route is preferred, and is assisted by a topical carrier. The topical carrier is one, which is generally suited for topical active ingredients administration and includes any such materials known in the art. The topical carrier is selected so as to provide the composition in the desired form, e.g., as a liquid or non-liquid carrier, lotion, cream, paste, gel, powder, ointment, solvent, liquid diluent, drops and the like, and may be comprised of a material of either naturally occurring or synthetic origin. It is essential, clearly, that the selected carrier does not adversely affect the active agent or other components of the topical formulation, and which is stable with respect to all components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Preferred formulations herein are colorless, odorless ointments, liquids, lotions, creams and gels.

Ointments are semisolid preparations, which are typically based on petrolatum or other petroleum derivatives. The specific ointment base to be used, as will be appreciated by those skilled in the art, is one that will provide for optimum active ingredients delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be made to Remington: The Science and Practice of Pharmacy for further information.

Lotions are preparations to be applied to the skin surface without friction, and are typically liquid or semi liquid preparations, in which solid particles, including the active agent, are present in a water or alcohol base. Lotions are usually suspensions of solids, and may comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Creams containing the selected active ingredients are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a nonionic, anionic, cationic or amphoteric surfactant.

Gel formulations are preferred for application to the scalp. As will be appreciated by those working in the field of topical active ingredients formulation, gels are semisolid, suspension-type systems. Single-phase gels contain organic macromolecules distributed substantially uniformly throughout the carrier liquid, which is typically aqueous, but also, preferably, contains an alcohol and, optionally, an oil.

Various additives, known to those skilled in the art, may be included in the topical formulations of the invention. For example, solvents may be used to solubilize certain active ingredients substances. Other optional additives include skin permeation enhancers, opacifiers, antioxidants, gelling agents, thickening agents, stabilizers, and the like.

The cosmetic compositions may contain one or more emulsifiers, preservatives, thickeners, sunscreens, antioxidants, emollients, skin protectants, hair protectants. Examples of excipients usually used in the cosmetic art may be added such as, but not limited to, methylparaben, glycerin, EDTA disodium, cetearyl alcohol, ceteareth 20, propylparaben, cetyl palmitate, steareth-20, octyl stearate, polyolprepolymer-2, lecithin, and the like.

The topical pharmaceutical compositions for the treatment of diabetic skin pathologies and disorders may contain other pharmaceutically active agents or ingredients, used for the treatment of such pathologies and disorders. Other agents may also be added, such as antimicrobial agents, antifungal agents, antibiotics and anti-inflammatory agents.

The topical cosmetic compositions for the prevention and/or treatment of diabetic and aging skin pathologies, disorders and conditions may contain additional nutrients used in anti-aging and anti-wrinkle compositions including, without limitation, Vitamins A, B, C, E and Panthenol.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Dosing is dependent on the type, the severity and manifestation of the pathology or disorder and on the responsiveness of the subject to the active ingredients, as well as the dosage form employed and the potency of the particular agent(s). The doses for cosmetic use, particularly for prevention purposes, will be usually lower than the doses for pharmaceutical/therapeutic purpose.

Diabetes and insulin resistance exert profound effects on skin architecture. Primarily, diabetic skin fails to present the hypodermis adipose layer; loss and irregularities of the subcutaneous adipose tissue modifies the compartmentalization of skin dermis and epidermis rendering the appearance of thinner skin. This manifestation is also characteristic of known diabetic skin pathologies such as Scleroderma Diabeticorum and leads to altered skin structure including skin thinning, flaky and dry skin, which also affect barrier function and skin elasticity. The significance of restoring the subcutaneous adipose tissue can indeed overcome many of the diabetic skin pathologies. This can be achieved according to the invention by treating diabetic skin with PKC modulating agents, various adipokines and insulin signaling related molecules, known to affect skin and adipose tissue differentiation and physiology.

In addition to the abrogation of the hypodermis subcutaneous adipose tissue, abnormal structure of the epidermis and the dermis layers is observed in diabetes skin. The diabetic epidermis is thin, exhibits fewer layers and portrays a disruption in differentiation pattern demonstrated by the increased cornified envelope formation. The impaired differentiation by itself is a common base for diabetic related dermopathies. Several skin pathologies of diabetic skin are related to the interference with normal epidermal structure such as Bullosis Diabeticorum, APD and others. Thus, by influencing the regulation of specific signaling pathways involved such as insulin, PKC and MAPK we can restore the normal differentiation pattern overcoming the epidermis related diabetic skin pathologies as demonstrated in Examples 10 and 13 hereinafter.

The loss of the hypodermis layer observed in the early stages of diabetes development leads also to the changes in matrix structure as we also demonstrate in Example 4. In diabetic skin the dermis appears to be disorganized and markedly reduced in size. Elastic fibers are reduced and matrix deposition is altered. These manifestations resemble human diabetic pathologies such as diabetic dermopathy and NLD. Furthermore, the proliferation capacity in diabetic skin is compromised underlying these pathologies. Restoration of the dermal layer, improved matrix deposition and skin strength can be achieved by induction of PKC modulating factors, insulin signaling related factors and adipokines as demonstrated in Example 8 hereinafter. This can also be achieved by induction of hypodermis adipose tissue formation. These results further demonstrate the importance of adipose tissue integrity and secreted factors to the correction of impairments characteristic of diabetes skin. Moreover, diabetic skin displays a tendency of an increased inflammatory response which also leads to severe complications in skin of diabetic patients. Utilization of PKC modulators can specifically and efficiently reduce the abnormal inflammatory response.

In light of the increase of the diabetic patient population, there is a strong need for the development of improved cosmetic compositions and cosmetic methods for the treatment and skin care of diabetes skin. As an alternative to existing products, the present invention further provides a method of providing at least one skin care benefit selected from the group consisting of: treating, delaying or preventing the impairments and pathologies which are characteristic of the diabetes state and improve the appearance and condition of skin. This includes: treating sensitive, dry or flaky skin, to induce skin elasticity and flexibility. Treating delaying or preventing sagging of skin; imparting a youthful appearance to skin, normalizing skin color by lightening or darkening skin; soothing irritated or sensitive skin; improving skin texture, enhancing skin smoothness and inducing skin firmness and strength as well as regulating oil/sebum secretion and moisture; Furthermore, these compositions are also indicated for delay, treat or prevent the distinct pathologies which can appear in diabetes skin including: necrobiosis lipoidica diabeticorum, granuloma annulare, diabetic dermopathy, bullosis diabeticorum, limited joint mobility, scleredema diabeticorum, acanthosis nigricans, acquired perforating dermatosis, insulin allergy or diabetes related cutaneous skin infections.

Many cosmetic compositions and cosmetic methods have been developed for skin care and treatment. However, regarding diabetic skin, a mechanism of action was not described and no specific compositions were found to specifically affect the impairment, associated with the distinct loss of structure and function, characteristic of the diabetes skin. Therefore, no unique products or treatment methods were described to date to treat the cosmetic appearance and the pathologies linked with skin diabetic state.

Overall, in this invention we show that diabetes skin has unique characteristics. We identified the mechanisms underlying the pathology and suggest a line of therapeutically active or cosmetically effective compositions for skin care in order to ameliorate or prevent the deterioration of skin structure in diabetes. Some of these compositions were shown to be effective in correcting unique defects correlated to the aging process as well. Therefore, they can be utilized as a new line of cosmetic care products treating the cosmetic appearance of aging skin. Overall, we show that specific molecules related to the insulin signaling pathway, MAPK signaling pathway, adipocyte secreted molecules and PKC modulating agents can treat, prevent or delay the impairments and pathologies of diabetic and aging skin as demonstrated in the presented examples.

The condition of human skin is affected by different factors such as humidity, ultraviolet rays, cosmetic compositions, aging, diseases, stress and nutrition. Several features are associated with skin aging. This includes loss of resilience and skin thinning which are associated with reduction in the number of cells and blood vessels that furnish the skin. In addition, aged skin is associated with changes in skin esthetics and appearance such as wrinkles and crow's feet, stains and age spots, sagging, loss of tautness and gloss, loss of flexibility and elasticity.

Decline in the fibroblasts and other dermal cells proliferation is associated with loss of collagen biosynthesis and irregularities of various components of the extracellular matrix in the skin thus, leading to loss of elasticity and induction of wrinkles and sagging which is characteristic of the skin aging process. Therefore, a variety of skin related products for cosmetic use in aging skin includes components known to affect dermal structure, dermal cell proliferation and the induction of collagen and matrix production. In the present invention, we have described a new mechanism for the induction of skin aging which is characterized by the loss of the subcutaneous fat tissue and mediates irregularities in the adipocyte tissue components within the skin, including the impairment in the secretion of various adipokines. In order to correct this phenomenon, known agents involved in the differentiation and distribution of adipose tissue were tested according to the invention. Our results show that treatment with these agents enhanced adipocyte distribution and hypodermis layer reformation/renewal in the damaged skin. These agents include PKC activators and inhibitors, factors which activate the insulin signaling pathway. In addition, as the subcutaneous fat tissue serves as an endocrine organ, pathologies could be overcome by the treatment of skin with a variety of adipose secreted factors, contributing to adipocyte proliferation and differentiation processes.

The cosmetic compositions and methods described herein result in the prevention, reduction or delay in the formation of wrinkles, the prevention, reduction or delay in loss of skin tone, and the prevention, reduction or delay in the formation of pimples and blackheads. They also moderate skin discolorations such as brown spots, age spots or liver spots, rejuvenate dry, abused, or irritated skin, close or tighten pores, improve skin texture, smoothness or firmness, and create smooth and supple skin with improved elasticity. A general improvement in the appearance, texture and condition, in particular with respect to the radiance, clarity, and general appearance of skin is achieved. The present invention therefore provides a wide range of results that are collectively described as anti-aging benefits.

The invention will now be illustrated by the following non-limiting Examples.

EXAMPLES

Material and Methods
(i) Materials.

Tissue culture media and serum were purchased from Biological Industries (Beit HaEmek, Israel). Enhanced Chemical Luminescence (ECL) was performed with a kit purchased from BioRad (Israel). Monoclonal anti phosphotyrosine antibody was purchased from Upstate Biotechnology Inc. (Lake Placid, N.Y., USA). Polyclonal and monoclonal antibodies to PKC isoforms were purchased from Santa Cruz (Calif., USA) and Transduction Laboratories (Lexington, Ky.). Rat mAB to phosphotyrosine was purchased from Sigma (St. Louis, Mo.) and rabbit anti phosphoserine was purchased from Zymed (San Francisco, Calif.). Horseradish peroxidase anti-rabbit and anti-mouse IgG were obtained from Bio-Rad (Israel). Leupeptin, aprotinin, phenylmethanesulfonyl fluoride (PMSF), dithiothreitol (DTT), Na orthovanadate and pepstatin were purchased from Sigma Chemicals (St. Louis, Mo.). Insulin (HumulinR, recombinant human insulin) was purchased from Eli Lilly France SA (Fergersheim, France). IGF1 was a gift from Cytolab (Israel). Keratin 1 and 14, and filaggrin antibodies were purchased from Babco-Convance (Richmond, Calif.).

(ii) Skin Damage In-Vivo Assays for Screening Compounds which Modify Skin Physiology Under Normal and Diabetic Conditions.

In order to identify the specific changes which characterize diabetic skin complications, we studied skin biopsies obtained from mice and Psammomys obesus animal models of diabetes type I and diabetes type II. Different mouse strains were used for the emphasis of specific signaling pathways. A wild type strain (129 brown mouse)—normal and diabetic sub groups. Mice were maintained normoglycemic or were diabetes-induced by a single injection of STZ (185 mg/kg in citrate buffer). In addition, we utilized an insulin signaling compromised strain and a defective MAPK signaling—normal and diabetic sub groups. Psammomys obesus were obtained from both diabetic prone and diabetic resistant strains and placed on high energy diet, which is the inducer of diabetes in this animal model. Skin biopsies were either embedded in paraffin or frozen for protein analysis via Western blotting. Assessment of specific parameters was performed by histological analysis using H&E, Elastin and Masson staining and immunohistochemistry specifically indicating epidermal differentiation state. Immunohistochemical markers included specific protein expression of keratins 14 and proliferating cell nuclear antigen (PCNA) characteristic of basal proliferating cells, Keratin 1 (specific of spinous differentiating cells) and filaggrin distribution (characteristic of the cornified layer-terminal differentiation state).

Our model of skin damage is based on late diabetic complications. We utilized a number of mouse models including C57BL/6J, known to spontaneously develop insulin resistance to some extent, together with streptozotocin (STZ) injection for diabetes development. Only mice that persisted to overt diabetes, assessed by the prolonged time with very high levels of hyperglycemia (>450 mg/dl for a period of 7 days or more), were taken into consideration and compared to their non-injected litter mates. Additional animal models included: a mouse with a defected insulin signaling pathway due to PKCδ depletion and a mouse from 129 origin with defective MAPK signaling route in skin due to PKCα depletion in skin. PKC downregulation can be achieved by either treating the skin with long term phorbol 12-myristate 13-acetate (PMA) exposure or the specific modulation of skin cells utilizing PKC isoform inhibitors. These mice were also injected with STZ and maintained in an overt diabetic state. Skin from these models was subjected to both paraffin embedding and histological analysis as well as protein expression analysis by immunoprecipitation and Western blot.

(iii) In Vitro Model Systems of Skin.

The in vitro model systems were based on primary skin cell cultures, either keratinocytes or fibroblasts. The cells were treated and tested for morphological changes as well as migratory and proliferative capacity. Migration was studied utilizing the scratch assay technique and proliferation was tested by proliferating cell nuclear antigen (PCNA) expression or by thymidine incorporation, as described by Shen et al. (2001).

(iv) Assessment of Scar Formation in Large White & Landrace Pig.

Incisions were performed on the backs of pigs and assessed for scar formation for periods of 20-30 days post-wounding. Biopsies were collected and embedded in paraffin. Assessment was performed by morphological and esthetics analysis.

(v) In Vitro Methods for the Detection of Compounds that Modulate Proliferation, Differentiation, Migration (Detachment, Attachment, Cell Death) of Keratinocytes and Dermal Fibroblasts.

Isolation and Culture of Murine Keratinocytes.

Primary keratinocytes were isolated from newborn skin as previously described (Alt et al., 2001). Keratinocytes were cultured in Eagle's Minimal Essential Medium (EMEM) containing 8% Chelex (Chelex-100, BioRad) treated fetal bovine serum. In order to maintain a proliferative basal cell phenotype, the final $Ca^{2+}$ concentration was adjusted to 0.05 mM. Experiments were performed 5-7 days after plating.

Isolation and Culture of Murine Dermal Fibroblasts.

Primary dermal fibroblasts were isolated from newborn skin. For each newborn skin, dermis was separated from epidermis after overnight flotation on trypsin. Dermises were then incubated with collagenase (25 ml per 10 dermises) for 30 min with agitation at 37° C. Next, 3 volumes of HiCa, namely, Dulbecco's Modified Eagle's Medium (DMEM) with serum and fungisome, were added to the filtrate and suspension was filtered through sterile nylon mesh and centrifuged at 1200 rpm for 7 min at RT (pellet contains fibroblasts and follicles). Pellet was re-suspended in HiCa, each mouse equivalent to 1 ml medium and centrifuged at 500 rpm for 3 min (pellet contains follicles; supernatant contains fibroblasts). Appropriate volumes of HiCa were added to the supernatant and plated in equivalent 1 mouse per 10 cm culture dish. The experiments were performed on early cell passages (passages 2-6).

Screening for Active Compounds that Affect Physiological Processes of Skin.

Once cells reached sub-confluency, their morphology was photodocumented (time zero) and treatment with different potential cosmeceutical agents was performed. The evaluation of the results was performed at appropriate time points: immediate molecular response 5 sec-15 min (for activation of molecular pathways) and late morphological/physiological response were assessed at 24-72 hours post-treatment. Morphological changes that are associated with maintenance of skin architecture (attachment/detachment, proliferation, differentiation, cell death) were followed and photodocumented. In addition, cell lysates were subjected to biochemical/molecular analysis using an appropriate method including immunoblotting with stage specific marker antibodies.

Preparation of Cell Extracts and Western Blot Analysis.

For crude membrane fractions, whole cell lysates were prepared by scraping cells into PBS containing 10 µg/ml aprotinin, 10 µg/ml leupeptin, 2 µg/ml pepstatin, 1 mM PMSF, 10 mM ethylenediaminetetraacetic acid (EDTA), 200 µM NaVO4 and 10 mM NaF. After homogenization and 4 freeze/thaw cycles, lysates were spun down at 4° C. for 20 min in a microcentrifuge at maximal speed. The supernatant containing the soluble cytosol protein fraction was transferred to another tube. The pellet was resuspended in 250 µl PBS containing 1% Triton X-100 with protease and phosphatase inhibitors, incubated for 30 min at 4° C. and spun down in a microcentrifuge at maximal speed at 4° C. The supernatant contains the membrane fraction. Protein concentrations were measured using a modified Lowery assay (Bio-Rad DC Protein Assay Kit). Western blot analysis of cellular protein fractions was carried out as described (Alt et al., 2001).

Preparation of Cell Lysates for Immunoprecipitation.

Culture dishes containing keratinocytes were washed with $Ca^{2+}/Mg^{2+}$-free PBS. Cells were mechanically detached in radioimmunoprecipitation (RIPA) buffer (50 mM Tris·HCl pH 7.4; 150 mM NaCl; 1 mM EDTA; 10 mM NaF; 1% Triton X-100; 0.1% SDS, 1% Sodium deoxycholate) containing a cocktail of protease and phosphatase inhibitors (20 µg/ml leupeptin; 10 µg/ml aprotinin; 0.1 mM PMSF; 1 mM DTT; 200 µM Na orthovanadate; 2 µg/ml pepstatin). The preparation was centrifuged in a microcentrifuge at maximal speed for 20 min at 4° C. The supernatant was used for immunoprecipitation.

Immunoprecipitation.

The lysate was precleared by mixing 300 µg of cell lysate with 25 µl of Protein A/G Sepharose (Santa Cruz, Calif., USA), and the suspension was rotated continuously for 30 mM at 4° C. The preparation was then centrifuged at maximal speed at 4° C. for 10 min, and 30 µl of A/G Sepharose was added to the supernatant along with specific polyclonal or monoclonal antibodies to the individual antigens (dilution 1:100). The samples were rotated overnight at 4° C. The suspension was then centrifuged at maximal speed for 10 min at 4° C., and the pellet was washed with RIPA buffer. The suspension was again centrifuged at 15,000×g (4° C. for 10 min) and washed 4 times in Tris-Buffered Saline Tween-20 (TBST). Sample buffer (0.5 M Tris·HCl pH 6.8; 10% SDS; 10% glycerol; 4% 2-beta-mercaptoethanol; 0.05% bromophenol blue) was added and the samples were boiled for 5 mM and then subjected to SDS-PAGE.

Example 1

Diabetes Skin Exhibits Excessive Inflammatory Response

One of the serious problems in skin that result from diabetes is the tendency of an abnormal upregulated inflammatory response. These hyperinflamed areas are future local 'hot spots' for skin susceptibility for diabetic lesions and further damage.

Skin biopsies of diabetic (STZ injected) as well as non-diabetic C57BL/6J mice were dissected and embedded in paraffin, and histological sections were performed and analyzed by H&E histological staining. Inflammation was graded by abscess formation and excessive leukocytosis in the skin and proximal blood vessels. FIG. 1A-1D show the inflammation response in skin of diabetic animals (1A-1B), in which abscess formation is marked by yellow arrows, vs. non-diabetic animals (1C-1D). As shown, skin of diabetic animals is indeed prone to severe inflammation response, indicated by facilitated abscess formation in different parts of the skin. Therefore, it is important to prevent this manifestation in order to overcome the diabetic inflamed skin problem.

In addition to the enhanced abnormal inflammatory response, the integrity of diabetic skin structure is severally compromised. This severe impairment includes the abrogation of the hypodermis subcutaneous adipose tissue, the hyper differentiation and abnormal structure of the epidermis, and the disruption of dermal structure.

Example 2

Skin Architecture is Altered in Diabetes and Aged Animals

Skin biopsies from normoglycemic as well as diabetic (STZ injected) C57BL/6J mice were paraffin embedded and analyzed by H&E histological staining.

Figure 2A:
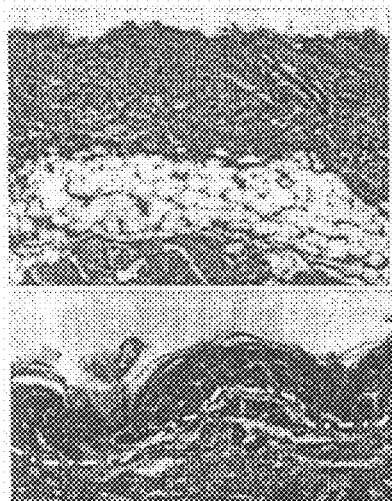
FIGS. 2A-2D demonstrate the structure of a normoglycemic mouse skin in which the hypodermis fat layer, indicated by an arrow, underlies the dermis (2A); the structure of a diabetic mouse skin exhibiting the absolute absence of the hypodermis fat tissue (2B); the structure of a normal mouse skin demonstrating normal arrangement of the epidermis underlined by a yellow speckled line (2C); and the structure of a diabetic mouse skin demonstrating abnormal organization of the epidermis underlined by a yelow speckled line (2D). Skin biopsies were dissected from either diabetic (STZ injected) or non-diabetic C57BL/6J mice, embedded in paraffin, and analyzed by H&E histological staining (Nikon Eclipse 50i microscope, 2A-2B-×10 magnification; 2C-2D-×40 magnification).
Figure 2B:
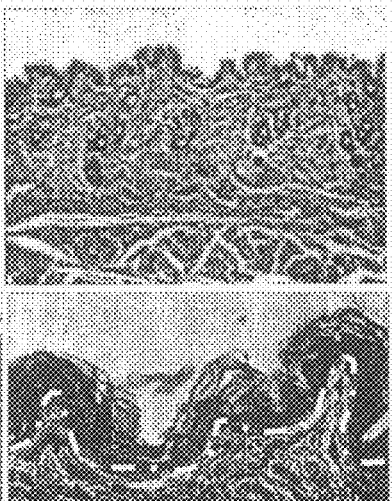
Figure 2C:
Figure 2D:

As shown in FIGS. 2A-2D, diabetes has a profound effect on skin architecture. FIG. 2A shows the structure of normoglycemic mouse skin in which the hypodermis fat layer, indicated by an arrow, underlies the dermis. Contrary to that, diabetic mouse skin exhibits an absolute absence of hypodermis fat tissue, and instead, the underlying muscle is "pushed" under the dermis rendering the appearance of thinner skin (FIG. 2B). The same phenomena was observed in all the other diabetic models we have tested, including the nonobese diabetic (NOD) mice, Psammomys obesus type 2 diabetic model, diabetic rats and also in large animal models. The restoration of the subcutaneous adipose tissue may overcome the diabetic skin pathologies. The epidermis is also compromised by the diabetic state. FIG. 2C shows the structure of normal mouse skin, demonstrating normal structure of the epidermis underlined by a yellow speckled line. FIG. 2D shows diabetic mouse skin demonstrating abnormal structure of the epidermis underlined by a yellow speckled line. As can be seen, the diabetic epidermis is thin, exhibits fewer layers and portrays a disruption in differentiation pattern demonstrated by an increased cornified envelope formation.

Skin biopsies from normal 129 brown mice as well as from impaired insulin signaling 129 brown mice, in which PKCδ deficiency was induced, were paraffin embedded and analyzed by H&E histological staining. FIGS. 3A-3B illustrate the direct effect of the insulin pathway on skin structure as demonstrated in the insulin resistant skin model (3B), exhibiting a defective dermal structure compared to the normal skin (3A). As shown in FIG. 3B, the dermis in the insulin resistant skin model appears to be markedly reduced as well as having a disorganized structure. The disorganized structure of the dermis is visible in whole animal observations as well: mice seem fragile with very thin skin. These pathologies resemble human diabetic pathologies such as diabetic dermopathy.

From the data presented above it is clear that diabetes affects all skin layers in a distinct manner. In addition, through utilization of the specific signaling models it is further understood that when the insulin signaling pathway is disrupted, the dermal layer is directly compromised. Thus, by modulating downstream elements of the insulin signaling pathway in skin such as PI3K, PDK1, MAPK, Ras, PKC, Akt and their adaptor molecules and transcription factors, we will be able to regulate architectural properties of skin. In addition, this data shows that the presence of the adipose layer is crucial for skin physiology. The importance of adipose tissue is further corroborated by the ability of fat cells to serve as a source of various secreted factors and as an endocrine organ (i.e. adipokine secretion), affecting other skin layers. Another aspect of diabetes induced architectural impairment is demonstrated by the epidermal differentiation scheme: by influencing the regulation of specific signaling pathways involved, such as insulin and MAPK, we can restore the normal differentiation pattern which is a common base for diabetic related dermopathies.

Eight weeks old and eight month old C57BL/6J mice (n=10 in each group) were sacrificed and skin biopsies were embedded in paraffin and analyzed by H&E histological staining for intact hypodermis layer. FIG. 4 shows the percent of mice with normal hypodermis in each group. As can be seen, old mice also exhibit depletion of the subcutaneous hypodermal layer, indicating that, as in diabetes, restoration of this layer will overcome the pathologies which result from its depletion.

Example 3

Skin Strength in Diabetic Animal

Diabetic skin has been described as frail and thin. Many of the pathologies related to the diabetic state have shown histological evidence of changes in matrix structure and physiology. We conducted a series of experiments following this basis and subjected skin biopsies to strength testing by bursting pressure. For this analysis, dissected skin was placed in a bursting chamber and increasing flow of $CO_2$ was inflicted on the skin. After the breaking point in which the skin was ruptured, the data was analyzed and summarized in graphic form.

Figure 5:
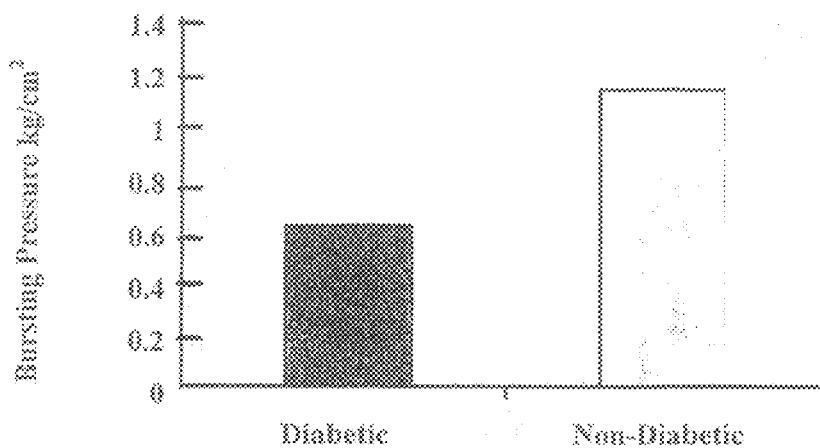
FIG. 5 shows the average skin strength and elasticity by evaluating bursting pressure (kg/cm$^2$) of skin biopsies dissected from either diabetic (STZ injected) or non-diabetic C57BL/6J mice where mice are treated as described in Example 3 hereinbelow (n=10 in each group).

Skin biopsies from diabetic (STZ injected) as well as non-diabetic C57BL/6J mice (n=10 in each group) were dissected and subjected to bursting pressure analysis, as described hereinabove. The bursting pressure ($kg/cm^2$) of each dissection is shown in Table 2 hereinbelow and the average bursting pressure of each group is shown in FIG. 5.

TABLE 2

Skin strength of diabetic (STZ injected) vs. non-diabetic mice

| Treatment | Skin Strength ($kg/cm^2$) |
|---|---|
| Non-Diabetic Mice | 0.85, 1.10, 1.25, 1.26, 1.28, 1.30, 1.40, 1.50, 1.52, 1.7 |
| Diabetic Mice | 0.10, 0.20, 0.25, 0.48, 0.55, 0.62, 0.64, 0.75, 0.82, 0.92, 1.2 |

As clearly shown in FIG. 5 and Table 2, skin strength is reduced by half in diabetic animals, further exemplifying the diabetic influence on skin structure. It is understood that skin strength is based on its collagen and other matrix fibers content and organization. Furthermore, as shown in Example 2 hereinabove, diabetic skin hypodermis layer is reduced promoting skin thinning and loss of skin strength. The restoration of skin strength can be achieved by influencing collagen and matrix fibers formation in the dermis, induction of hypodermis adipose tissue formation and distribution, as well as maintenance of adequate epidermal organization (proliferation and differentiation patterns).

Example 4

Skin Elasticity and Diabetes

Skin biopsies from diabetic (STZ injected) C57BL/6J mice were paraffin embedded and analyzed by elastin staining using the Verhoeff-Van Gieson procedure for elastic fibers, described by Fan and Nagle (2002).

Figure 6A:
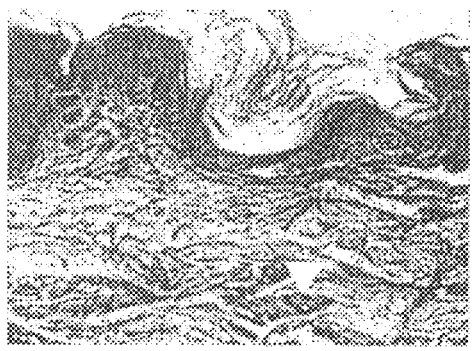
FIGS. 6A-6C show elastin distribution (illustrated as thin black fibers outlined by yellow arrows) of diabetic mouse skin (6A); diabetic mouse skin following manipulation by induction of MAPK pathway, exhibiting restoration of elastic fibers (6B); and diabetic mouse skin in which insulin signaling was impaired by inhibition of PKCδ activation where elastic fibers distribution was scarce (6C). Skin biopsies were dissected from diabetic (STZ injected) C57BL/6J mice, embedded in paraffin, and analyzed by Elasthin staining using the Verhoeff-Van Gieson procedure for elastic fibers (×40 magnification Nikon Eclipse 50i microscope).
Figure 6B:
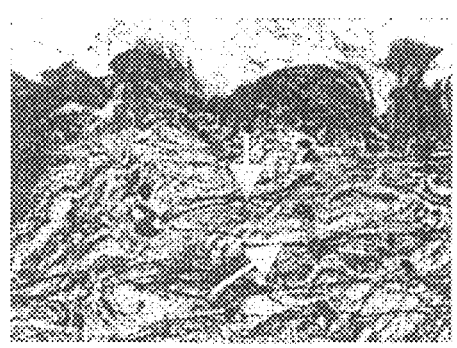
Figure 6C:
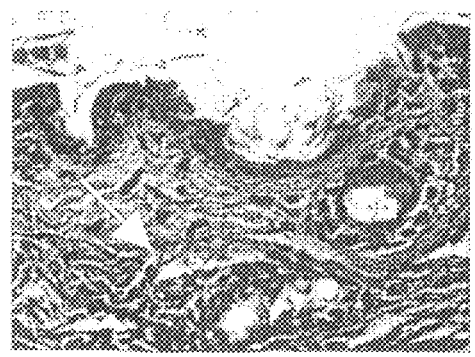

FIGS. 6A-6C show the elastin distribution in the various skin biopsies illustrated as thin black fibers outlined by yellow arrows: FIG. 6A shows the elastin distribution in diabetic mouse skin, FIG. 6B shows diabetic mouse skin following manipulation by induction of MAPK pathway, exhibiting restoration of elastic fibers, and FIG. 6C shows diabetic mouse skin in which insulin signaling was impaired by inhibition of PKCδ activation, exhibiting a similar pattern of proliferation as the diabetic control (6A).

In addition to the disrupted skin architecture and reduced skin strength, diabetic skin has been shown to be more fragile due to loss of elastic filaments. The data presented hereinabove clearly demonstrate that diabetic skin has reduced elastin fiber distribution in the dermis, and through the signaling specific models we better understand this phenomenon. In the insulin signaling defective skin model shown in FIG. 6C, elastin fibers seem to be decreased under diabetic condition as compared to wild type normoglycemic controls (not shown), indicating that insulin signaling has a direct influence on elastin content. On the other hand, the MAPK regulated pathway model, shown in FIG. 6B, restores elastin content to normoglycemic levels (not shown), indicating that by overriding the insulin non-responsive pathway by activating downstream elements in various ways we can treat diabetes related skin impairments.

Example 5

Diabetes Influences Proliferation Capacity of Skin

Skin biopsies from normoglycemic as well as diabetic (STZ injected) C57BL/6J mice were paraffin embedded and analyzed by proliferating cell nuclear antigen (PCNA) immunohistochemical staining.

Figure 7A:
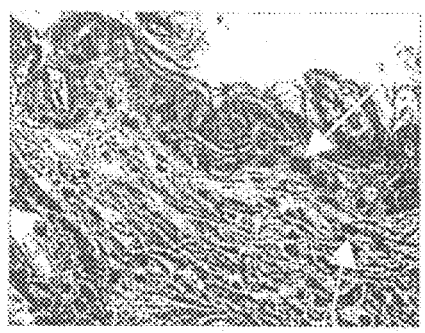
FIGS. 7A-7C show skin proliferation capacity of (i) normoglycemic mouse skin illustrated as dark brown stained nuclei, outlined by yellow arrows (7A); (ii) diabetic mouse skin exhibiting marked reduction in the skin proliferating capacity (less brown staining) both in dermis and epidermis (7B); and (iii) diabetic mouse skin in which MAPK and PKCα pathways were inhibited, exhibiting restoration of normal proliferation capacity outlined by yellow arrows (7C). Skin biopsies were dissected from either diabetic (STZ injected) or non-diabetic C57BL/6J mice, embedded in paraffin, and analyzed by proliferating cell nuclear antigen (PCNA) immunohistochemical staining (×40 magnification Nikon Eclipse 50i microscope).
Figure 7B:
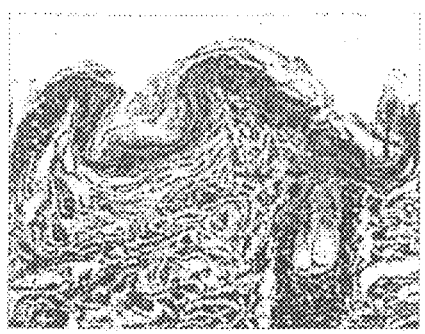
Figure 7C:
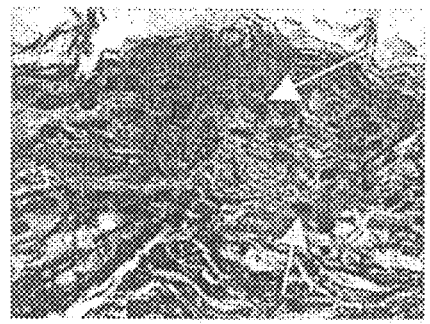

FIGS. 7A-7C show the proliferation capacity of the various skin biopsies illustrated as dark brown stained nuclei: FIG. 7A shows the proliferation capacity of normoglycemic mouse skin illustrated as dark brown stained nuclei outlined by yellow arrows; FIG. 7B shows diabetic mouse skin exhibiting marked reduction in the skin proliferating capacity (less brown staining) both in dermis and epidermis; and FIG. 7C shows diabetic mouse skin in which MAPK and PKCα pathways were inhibited, exhibiting restoration of normal proliferation capacity outlined by yellow arrows.

It is well documented that the proliferation capacity in diabetic skin is compromised underlying many related pathologies such as acanthosis nigricans, acquired perforating dermatosis (APD) and other dermopathies. The data presented hereinabove illustrates that diabetes down regulates proliferation in the epidermis as well as in the dermis. Through the manipulation of specific signaling pathways, including insulin down stream signaling such as MAPK and PKCα mediated pathways, we can restore the proliferation pattern both in the normal and diabetic animals (FIG. 7C). These results imply that by inhibiting specific elements of the MAPK pathway and specific regulation of insulin downstream signaling we can overcome the defects associated with signaling related skin pathologies involving epidermis and/or dermis and for hypodermis proliferation and differentiation.

In order to prevent and treat the impairments and pathologies of diabetic skin, specific molecules related to the insulin signaling pathway or the MAPK signaling pathway, adipocyte secreted molecules, PKC modulating agents and other related molecules can be used, as demonstrated in the following examples.

Example 6

Attenuation of the Diabetic Skin Inflammatory Response

Figure 8:
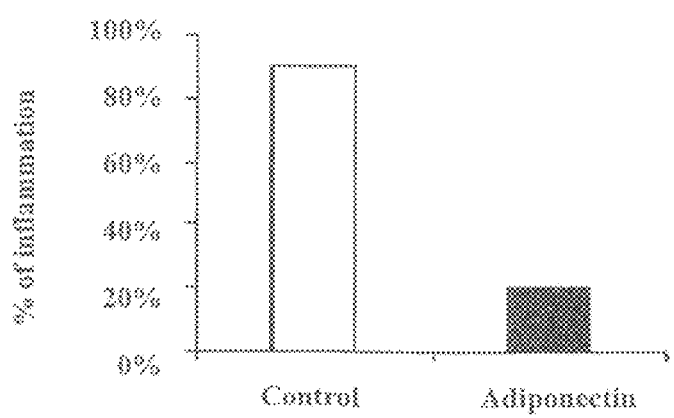
FIG. 8 shows the percent of diabetic (STZ injected) C57BL/6J mice treated with either PBS (control) or adiponectin (0.1 µg/ml) for 7 days, exhibiting severe inflammation, where treatment with adiponectin was able to diminish the inflammatory response graded by both abscess formation and excessive leukocytosis in the skin and proximal blood vessels. Skin biopsies were dissected, embedded in paraffin, and analyzed by H&E histological staining (total n=18).

Damaged skin of diabetic (STZ injected) C57BL/6J mice was treated with either PBS (control) or adiponectin (0.1 µg/ml) for 7 days (total n=18). Thereafter, skin biopsies were collected, embedded in paraffin, and analyzed for inflammation by H&E histological staining. Inflammation was graded by abscess formation and excessive leukocytosis in the skin and proximal blood vessels, and severe inflammation was considered when both abscess and leukocytosis were apparent. FIG. 8 shows the percent of total animals per group with severe inflammation.

Figure 9:
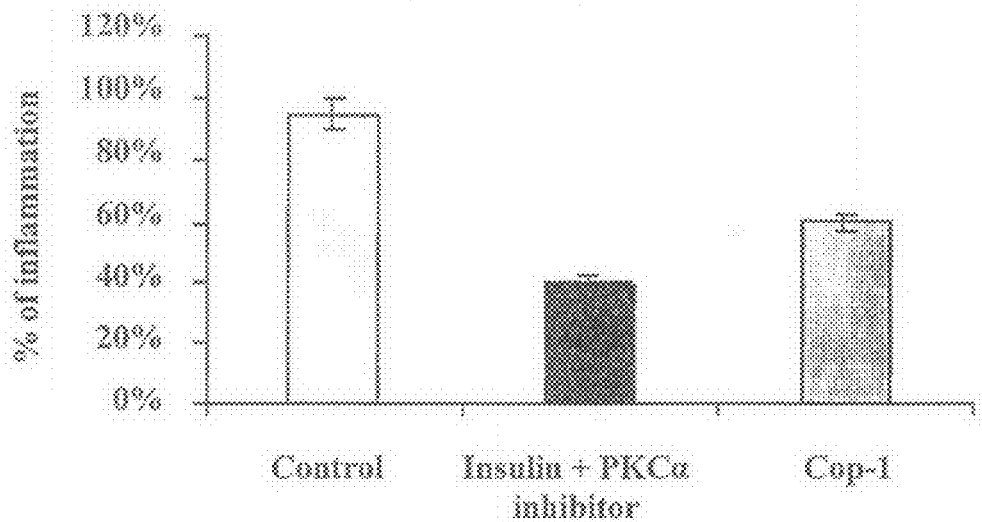
FIG. 9 shows the percent of diabetic (STZ injected) C57BL/6J mice treated with: (i) PBS (control); (ii) a mixture of insulin (0.1 unit) and the N-myristoylated PKCα pseudosubstrate peptide of SEQ ID NO: 1 (1 µM) (insulin+PKCα inhibitor); or (iii) Cop-1 (55 µg/ml), for 9 days, exhibiting severe inflammation. Both treatment with insulin and PKCα inhibitor as well as with Cop-1 were able to eliminate the inflammatory response, graded by both abscess formation and excessive leukocytosis in the skin and proximal blood vessels. Skin biopsies were dissected, embedded in paraffin, and analyzed by H&E histological staining (n=6 per each group).

In the next step, damaged skin from diabetic (STZ injected) C57BL/6J mice was treated with either PBS (control); a mixture of insulin (0.1 unit) and the N-myristoylated PKCα pseudosubstrate peptide of SEQ ID NO: 1 (1 µM); or Copolymer-1 (Teva Pharmaceutical Industries, Israel), (55 µg/ml) for 9 days (n=6 per each group). As previously discovered in the laboratories of the present inventors, Cop-1 was found to be a specific and very effective PKCη inhibitor. Thereafter, skin biopsies were collected, embedded in paraffin, and analyzed for inflammation by H&E histological staining. Inflammation was graded as described above. FIG. 9 shows the percent of total animals per group with severe inflammation.

FIG. 8 shows that the hyperinflammation phenomenon in diabetic skin can be prevented by introducing adipokines such as adiponectin. In particular, adiponectin at 0.1 µg/ml dramatically reduced the inflammation response in skin where only 20% of the animals exhibited severe inflammation of the skin in comparison to 90% in the non-treated control group. Similar results were obtained when different adiponectin concentrations (0.01-1 µg/ml) were tested (not shown).

FIG. 9 shows that the hyperinflammation can be reduced when treating with either specific peptides such as PKCη inhibitors or peptide combinations such as the combination of a PKCα inhibitor and insulin which is a PKCδ activator. In particular, a markedly reduced inflammation was achieved when treating with either Cop-1 or the combination of insulin and the N-myristoylated PKCα pseudosubstrate peptide of SEQ ID NO: 1.

Example 7

Agents Increasing Skin Strength in Diabetic Mice

Figure 10:
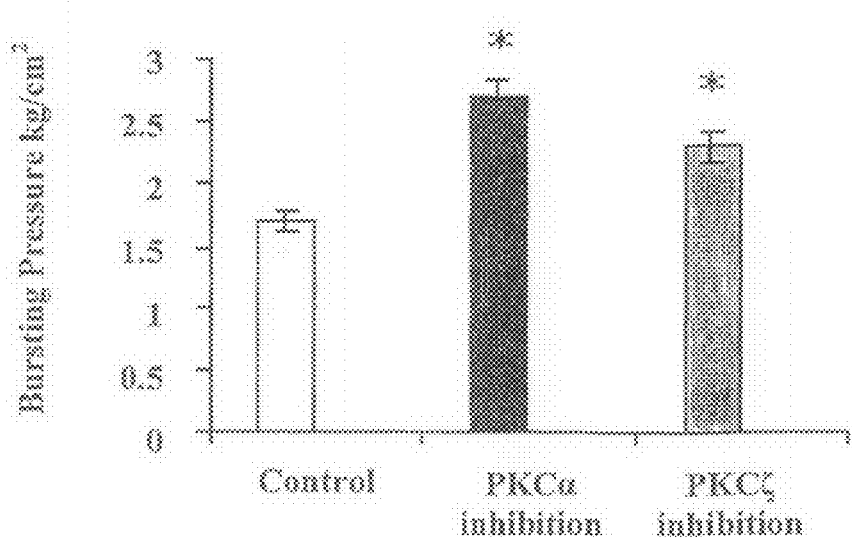
FIG. 10 shows the average bursting pressure (kg/cm$^2$) of skin biopsies dissected from: (i) 129 wild type mice (control); (ii) 129 PKCα deficient mice; or (iii) 129 PKCζ deficient mice, and treated as described in Example 3 hereinbelow.

Skin biopsies from 129 wild type mice and from 129 where PKCα or PKCζ activation was depleted, were dissected and subjected to bursting pressure analysis, as described in Example 3 hereinabove. The average bursting pressure (kg/cm$^2$) per group is shown in FIG. 10.

As can be seen, specific modulation of signaling pathways known to influence matrix and collagen formation, adipose tissue differentiation and epidermal integrity in skin can improve skin strength. Skin strength in diabetic animals is impaired, as a result of impaired skin regeneration of the various skin layers affecting related physiological processes. These results point out potential treatments overcoming diabetic related impairments.

Example 8

Reconstruction of the Hypodermis Layer in Damaged Skin

Figure 11A:
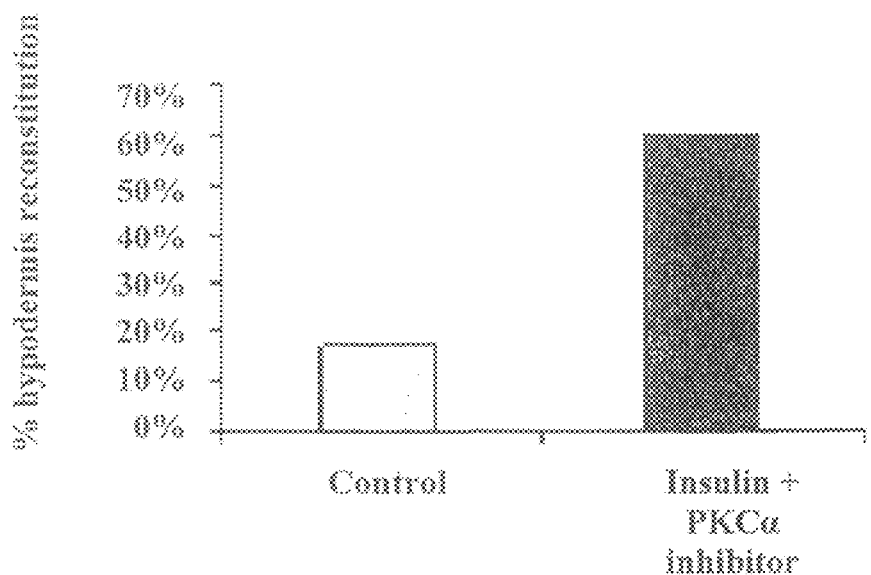
FIGS. 11A-11B show the percent of hypodermis reconstitution in skin biopsies dissected from diabetic (STZ injected) C57BL/6J mice after 7-9 days of treatment with: (i) either PBS (control) or the combination of insulin (0.1 unit) and the N-myristoylated PKCα pseudosubstrate peptide of SEQ ID NO: 1 (1 µM) (insulin+PKCα inhibitor) (11A); or (ii) either PBS (control) or adipsin (1 µM) (11B). These results demonstrate the ability of insulin, PKC modulators and adipocyte secreted factors to induce subcutaneous fat cell deposition and hypodermal layer distribution in diabetic skin. Skin biopsies were then dissected, embedded in paraffin, and analyzed by H&E histological staining.
Figure 11B:
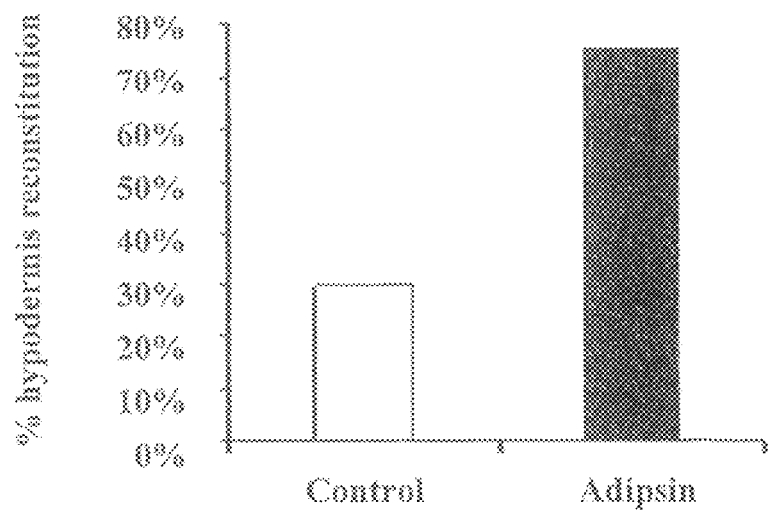

Damaged skin from diabetic (STZ injected) C57BL/6J mice was treated with either PBS (control); a mixture of insulin (0.1 unit) and the N-myristoylated PKCα pseudosubstrate peptide of SEQ ID NO: 1 (1 µM); or adipsin (1 µM) for 7-9 days. Skin biopsies were then collected and embedded in paraffin, and histological sections were performed and stained with H&E. The sections were analyzed for presence of the hypodermis layer presented as a continuous layer of adipocytes, and the percent of total animals per each group with fully reconstituted hypodermis is shown in FIGS. 11A-11B.

The results presented hereinabove clearly demonstrate that the combination of a PKCα inhibitor such as the N-myristoylated PKCα pseudosubstrate peptide of SEQ ID NO: 1 and a PKCδ activator such as insulin, as well as adipokines such as adipsin, can reconstruct the hypodermal subcutaneous layer in diabetic animal and prevent some of the severe diabetic skin impairments.

Example 9

Effect of Various Agents Including Thiazolidinediones (TZDs) and PKC Modulators on Regeneration of the Epidermis in Insulin Resistant Skin Primary mouse keratinocytes were cultured in 0.05 mM $Ca^{+2}$ MEM and differentiation was induced by elevating $Ca^{+2}$ concentrations to 0.12 mM. Keratinocytes were treated with either PBS (control) or different concentrations (50, 150 and 300 nM) of troglitazone, a PPARγ activator. The cells were lysed and the cytoskeletal fraction was subjected to SDS-PAGE and blotted with anti-filaggrin antibody.

Figure 12:
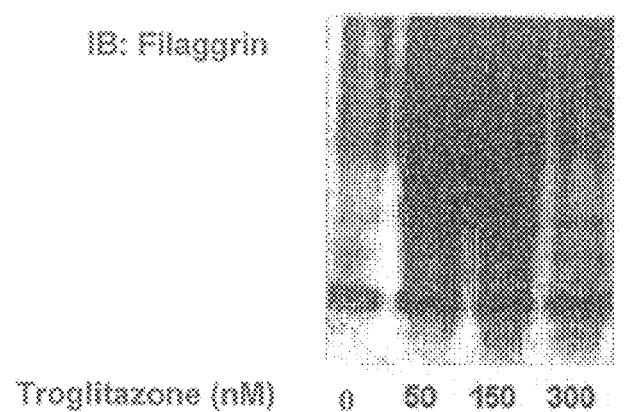
FIG. 12 shows the analysis of the cytoskeletal fraction obtained from primary keratinocytes, cultured in 0.12 mM Ca$^{+2}$ and treated with different concentrations (0, 50, 150 and 300 nM) of troglitazone, after it was subjected to SDS-PAGE and Western blot analysis utilizing anti-filaggrin antibody.

PPARγ is an insulin regulated transcription factor mainly secreted by adipocytes, and a crucial regulator of diabetes progression. PPARγ can affect keratinocytes underlined by subcutaneous adipose tissue. As clearly shown in the Western blot analysis, activation of PPARγ can induce the pattern and structure of normal skin by upregulation of filaggrin expression which signifies induction of terminal differentiation and cornified layer formation (FIG. 12).

Figure 13:
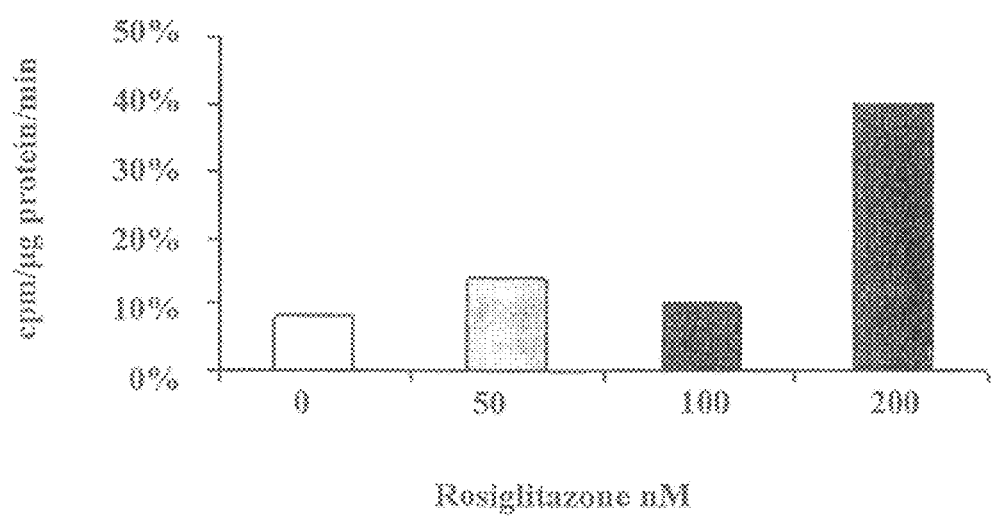
FIG. 13 shows the proliferation analysis of primary keratinocytes treated with different concentrations (0, 50, 100 and 200 nM) of rosiglitazone, analyzed by thymidine incorporation as described in Material and Methods hereinafter. The thymidine incorporation was measured in cpm/µg protein/min.

In the next step, 5-day old primary mouse keratinocytes were untreated or treated for 20 min with different concentrations (50, 100 and 200 nM) of rosiglitazone, another PPARγ agonist known as an anti-diabetic drug. The cells were then washed with PBS (×2) and culture medium was added. Eighteen hours after treatment, the cells were subjected to proliferation analysis by thymidine incorporation, as described in Materials and Methods hereinabove. FIG. 13 shows the effect of rosiglitazone on keratinocyte proliferation capacity. The results show the profound increase in keratinocyte proliferation by rosiglitazone, further acknowledging the role of adipocyte secreted factors on skin physiology.

Keratin 1 (K1) belongs to a large family of cytoskeletal proteins whose expression in skin keratinocytes varies depending on commitment of the cell to differentiate into spinous epidermal layer. Reduced K1 expression leads to skin hyperplasia, callus formation and disruption of skin barrier functions.

Figure 14:
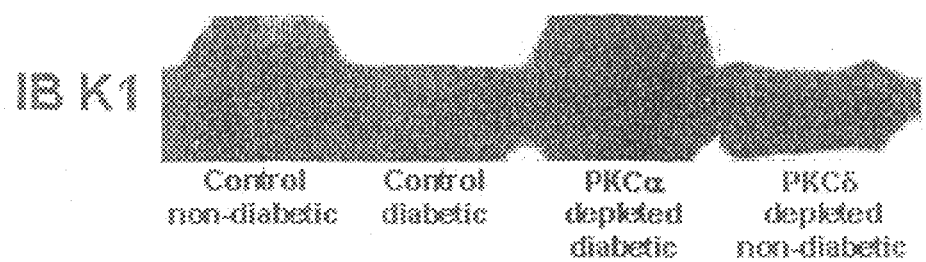
FIG. 14 shows the analysis of cytoskeletal fractions of whole skin total lysates from: (i) a control non-diaetic; (ii) a control diaetic; (iii) a PKCα depleted diabetic; and (iv) a PKCδ depleted non-diabetic 129 brown mice, subjected to Western-Blot analysis utilizing anti-K1 antibody.

Cytoskeletal fractions of whole skin total lysates from various experimental mice were subjected to Western blot analysis utilizing anti-K1 antibody. As shown in FIG. 14, skin from diabetic mice exhibits reduced K1 expression, supporting earlier observations of diabetes-related skin complications. Diabetic animals with depleted PKCα levels demonstrates high levels of epidermal K1, similarly to those observed in control non-diabetic animals. In contrast, PKCδ depletion causes reduction of K1 expression in skin of non-diabetic animals. The data presented above indicate that prevention of K1 decrease in skin by PKCα inhibition or by upregulation of PKCδ activity, together with pharmacological maintenance of K1 expression, may minimize diabetes-related damages in skin.

Example 10

Figure 15:
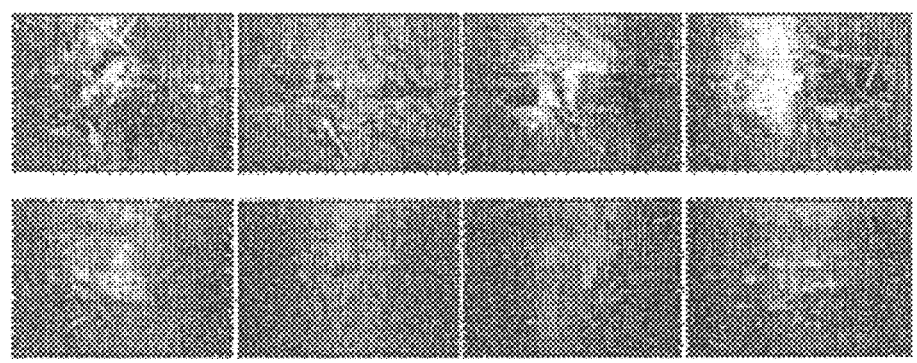
FIG. 15 shows scar sites, resulted from the closure of surgical incisions performed on the backs of Large-whitex & Landrace 4 month old 60 kg female pigs (n=8), treated with either PBS (upper panel) or the combination of insulin and the N-myristoylated PKCα pseudosubstrate peptide of SEQ ID NO: 1.

The Combination of Insulin and a PKCα Inhibitor Prevents Scar Formation and Improves Esthetics of a Damaged Skin In Vivo Surgical longitudinal incisions were performed on the backs of Large White & Landrace 4 month old 60 kg female pigs (n=8). After wound closure, the scar sites were treated with either PBS (control) or with the combination of insulin (0.1 unit) and the N-myristoylated PKCα pseudosubstrate peptide of SEQ ID NO: 1 (1 µM) for 21 days. Thereafter, the scar sites were photographed for the assessment of esthetics and scar formation. FIG. 15 shows the 4 scar sites treated with PBS (upper panel) and the 4 scar sites treated with the combination described above (lower panel).

Figures 16A, 16B:
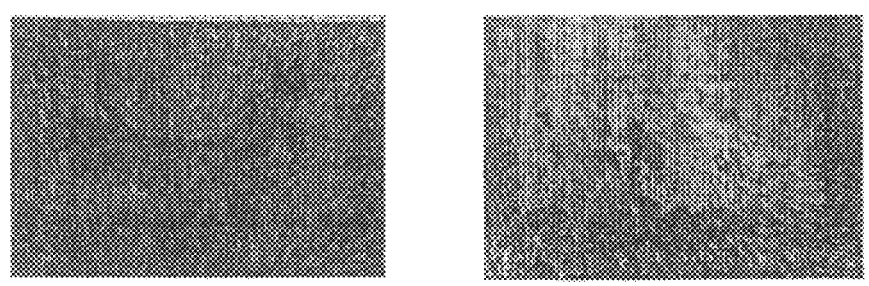
FIGS. 16A-16B show a scared horse skin before (16A) and after 14 days of topical treatment with the combination of insulin (0.1 unit) and the N-myristoylated PKCα pseudosubstrate peptide of SEQ ID NO: 1 (1 μM) (16B).

In a different experiment, scarred horse skin was treated topically for 14 days with the combination described hereinabove, in order to improve the esthetics of the skin. FIG. 16 shows the treated area on days 0 (16A) and 14 (16B).

As clearly shown in both FIGS. 15 and 16, the treatment with the combination of insulin and the N-myristoylated PKCα pseudosubstrate peptide of SEQ ID NO: 1, affecting the insulin-MAPK signaling pathway, can prevent scar formation and improve the overall esthetics of a damaged skin. Furthermore, in large animals including horses and dogs, treatment also induced the growth and development of new hair in replacement of scar tissue implying the ability of treatment to induce hair growth, which further improves skin aesthetics, indicating that the same effect may also be achieved by other small molecules affecting the insulin-MAPK signaling pathway.

Example 11

Figure 17:
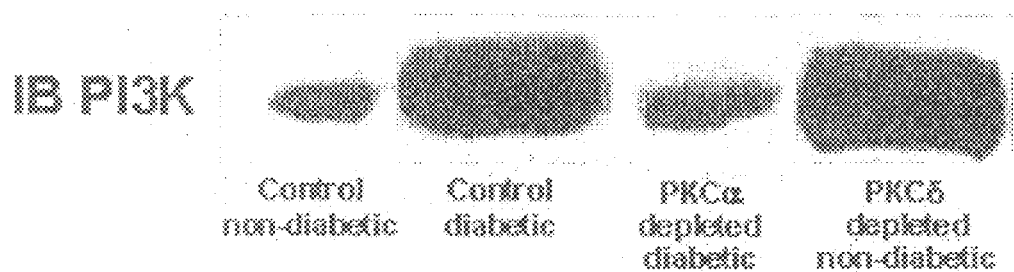
FIG. 17 shows the analysis of Triton-soluble fractions of whole skin total lysates from various experimental 129 brown mice (a control non-diabetic; a control diabetic; a PKCα depleted diabetic; and a PKCδ depleted non-diabetic), subjected to Western Blot analysis utilizing anti-PI3K antibody.

Mediators of the Insulin Signaling Pathway can be Modulated to Prevent and/or Overcome Diabetes Skin Pathologies Phosphotidylinositol-3-Kinase (PI3K) is known as one of the keystones of insulin signaling. It functions upstream of Akt and delivers the signal from insulin receptor via phosphotidylinositol-3-phosphates. FIG. 17 shows the analysis of Triton-soluble fractions of whole skin total lysates from (i) a control non-diabetic; (ii) a control diabetic; (iii) a PKCα depleted diabetic; and (iv) a PKCδ depleted non-diabetic 129 brown mice, subjected to Western blot analysis utilizing anti-PI3K antibody. As shown, a drastic elevation in PI3K expression levels in skin of diabetic mice is observed, probably due to compensatory mechanism of the skin. PKCα depletion in diabetic animals normalized PI3K expression and brought its levels to those of control non-diabetic mice. This was associated with restoration of normal histological features in skin as observed by histology slides. Moreover, mice lacking PKCδ, even at the non-diabetic state, demonstrated extremely high levels of PI3K, higher than those observed in control diabetic animals, predisposing the experimental animals to diabetes complications. These skins were also depleted of adipose tissue and demonstrated thinning of skin (not shown). Thus, inhibition of PI3K expression by pharmacological agents together with PKCα activity downregulation may benefit diabetes-related complications in skin.

Figure 18A:
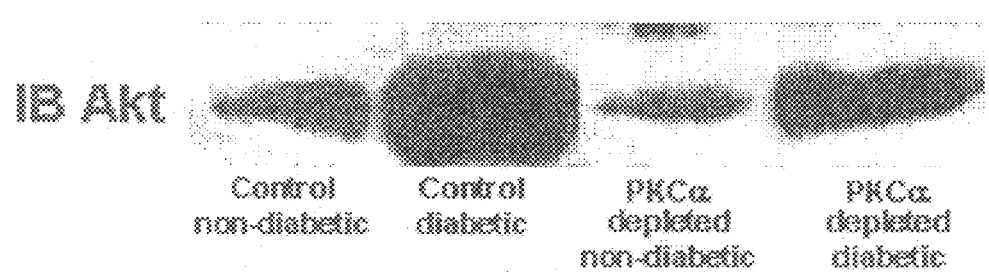
FIGS. 18A-18B show the analysis of Triton-soluble fractions of whole skin total lysates from various experimental 129 brown mice (a control non-diabetic; a control diabetic; a PKCα depleted non-diabetic; and a PKCα depleted diabetic), subjected to Western blot analysis utilizing anti-Akt antibody (18A), and the analysis of Triton-soluble fractions of whole skin total lysates from various experimental 129 brown mice (a control non-diabetic; a PKCα depleted non-diabetic; and a PKCδ depleted non-diabetic), subjected to Western blot analysis utilizing anti-pThrAkt antibody (18B).
Figure 18B:
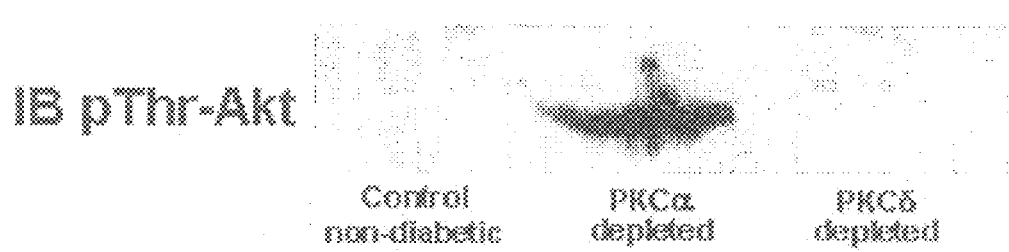

As a result of insulin induced signaling, key enzyme Akt becomes activated and initiates various cellular responses that include differentiation, migration and survival. Akt represents one of the hallmarks of PI3K-mediated insulin signaling. Its regulation by altering its cellular expression may contribute to insulin sensitivity of the cell. FIG. 18A shows the analysis of Triton-soluble fractions of whole skin total lysates from (i) a control non-diabetic; (ii) a control diabetic; (iii) a PKCα depleted non-diabetic; and (iv) a PKCα depleted diabetic 129 brown mice, subjected to Western blot analysis utilizing anti-Akt antibody. As can be seen, expression level of Akt significantly increases in skin of diabetic mice as compared to non-diabetic animals. This may be attributed to the loss of this enzyme activation due to lack of insulin in diabetic animals and accumulation of unused Akt potential as a compensation mechanism by the cell. PKCα deficient non-diabetic mice exhibit Akt levels similar to control; however, induction of diabetes in these animals eventually elevates Akt expression levels, though significantly lower intensity. As shown in FIG. 18B, this can be explained by basal elevation of Akt activity in PKCα deficient animals, which in turn downregulates Akt expression by inducing Aid inhibiting proteins.

The data presented hereinabove indicate that inhibition of PKCα minimizes the diabetes-related effect on Akt expression levels in skin. Taken together with pharmacological prevention of Akt accumulation, PKCα inhibition will contribute to normalization of Akt levels in skin cells of diabetic patients.

Figure 19:
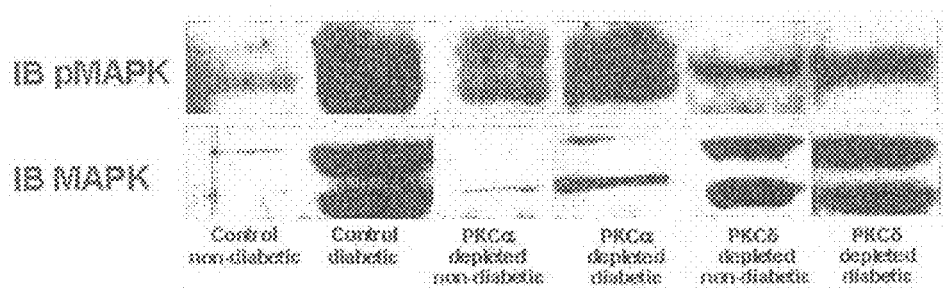
FIG. 19 shows the analysis of Triton-soluble fractions of whole skin total lysates from various experimental 129 brown mice (a control non-diabetic; a control diabetic; a PKCα depleted non-diabetic; a PKCα depleted diabetic; a PKCδ depleted non-diabetic; and a PKCδ depleted diabetic), subjected to Western Blot analysis utilizing anti-pMAPK and anti-MAPK antibodies.

Similarly to Akt, another signaling component of insulin-induced pathways, MAPK, is activated in response to insulin. FIG. 19 shows the analysis of Triton-soluble fractions of whole skin total lysates from (i) a control non-diabetic; (ii) a control diabetic; (iii) a PKCα depleted non-diabetic; (iv) a PKCα depleted diabetic; (v) a PKCδ depleted non-diabetic; and (vi) a PKCδ depleted 129 brown diabetic mice, subjected to Western Blot analysis utilizing anti-pMAPK and anti-MAPK antibodies.

As shown in FIG. 19, induction of diabetes elevates both MAPK activation and cellular expression levels. In PKCα deficient animals, activation and expression of MAPK show only a minor increase. Thus, inhibition of PKCα prevents MAPK accumulation and activation and therefore balancing MAPK distribution in diabetes patients. On the other hand, PKCδ deficient mice show relatively high levels of MAPK activation and expression even at non-diabetic conditions, thus predisposing the animal to diabetes development. The data presented hereinabove indicate that by inhibiting PKCα and activation of PKCδ, together with pharmacological inhibition of MAPK activation and/or expression, one may overcome diabetes symptoms in skin.

Example 12

Figure 20A:
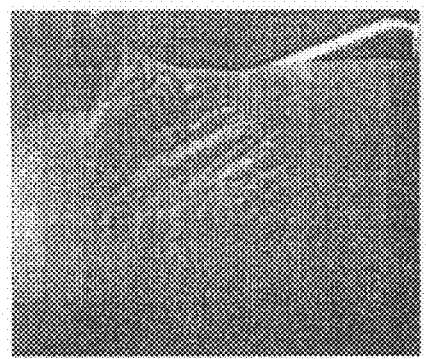
FIGS. 20A-20B show a palm with flaky skin on the hand of a patient with diabetes related skin disorder, before (20A) and after 14 days of topical treatment with the combination of insulin (0.1 unit) and the N-myristoylated PKCα pseudosubstrate peptide of SEQ ID NO: 1 (1 μM) (20B).
Figure 20B:
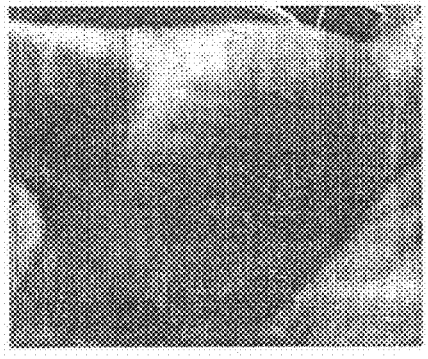

The Combination of Insulin with a PKCα Inhibitor Promotes Complete Recovery of Diabetes Related Skin Disorders A patient with diabetes related skin disorder was treated topically with a combination of insulin (0.1 unit) and the N-myristoylated PKCα pseudosubstrate peptide of SEQ ID NO: 1 (1 µM). FIGS. 20A-20B show the palm of the hand of this patient on days 0 (20A) and 14 (20B).

Figure 21A:
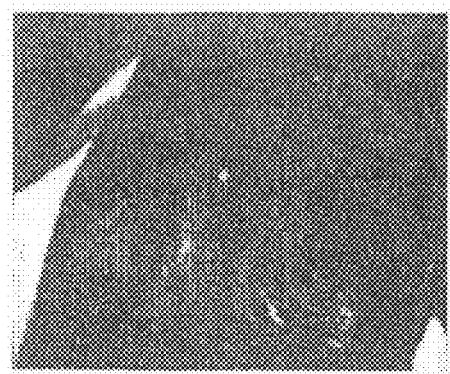
FIGS. 21A-21B show the back of the hand of an 80 year old patient, with diabetes related skin diabetic dermopathy, before (21A) and after 14 days of topical treatment with the combination of insulin (0.1 unit) and the N-myristoylated PKCα pseudosubstrate peptide of SEQ ID NO: 1 (1 μM) (21B).
Figure 21B:
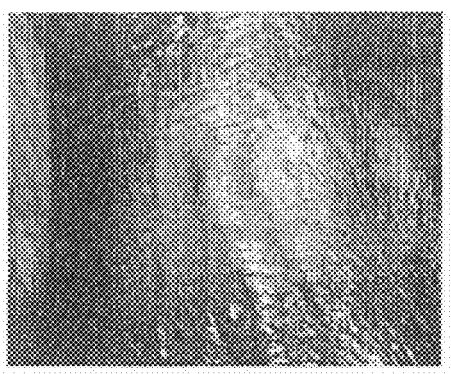

Another aging patient (80 years old) with diabetes dermopathy was treated as described hereinabove. FIGS. 21A-21B show the back of the hand of this patient on days 0 (21A) and 14 (21B).

Figure 22A:
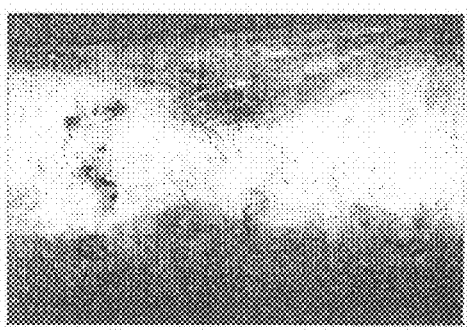
FIGS. 22A-22B show the diabetic lesions of an 83 year old patient, before (22A) and after 14 days of topical treatment with the combination of insulin (0.1 unit) and the N-myristoylated PKCα pseudosubstrate peptide of SEQ ID NO: 1 (1 μM) (22B).
Figure 22B:
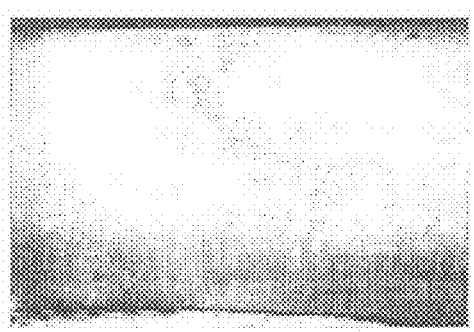

In the third case, diabetic lesions of a patient were treated for 14 days as described above. FIG. 22A-22B show the treated area on days 0 (22A) and 14 (22B).

The results presented hereinabove indicate that in all these cases, a two weeks treatment with the aforesaid combination promoted complete recovery of the skin.

REFERENCES

Alt, A. Ohba, M. Li, L. Gartsbein, M. Belanger, A. Denning, M. F. Kuroki, T. Yuspa, S. H. Tennenbaum, T., Protein kinase Cdelta-mediated phosphorylation of alpha6beta4 is associated with reduced integrin localization to the hemidesmosome and decreased keratinocyte attachment, *Cancer Res.*, 2001, 61, 4591-4598

Benes, C. H. Wu, N. Elia, A. E. H. Dharia, T. Cantley, L. C. Soltoff, S. P., The C2 domain of PKCδ is a phosphotyrosine binding domain, *Cell*, 2005, 121, 271-280

Chang, L. Chiang, S. H. Saltiel, A. R., Insulin signaling and the regulation of glucose transport, *Mol Med.*, 2004, 10 65-71

Connery, L. E. Coursin, D. B., Assessment and therapy of selected endocrine disorders, *Anesthesiol. Clin. North America*, 2004, 22, 93-123

Elias, P. M. Ghadially, R., The aged epidermal permeability barrier: basis for functional abnormalities, *Clin Geriatr Med.*, 2002, 18, 103-120

Farese, R. V. Sajan, M. P. Standaert, M. L., Insulin-sensitive protein kinases (atypical protein kinase C and protein kinase B/Akt): actions and defects in obesity and type II diabetes, *Exp Biol Med.*, 2005, 230, 593-605

Fliers, E. Kreier, F. Voshol, P. J. Havekes, L. M. Sauerwein, H. P. Kalsbeek, A. Buijs, R. M. Romijn, J. A., White adipose tissue: getting nervous, *J Neuroendocrinol.*, 2003, 15, 1005-1010

Formisano, P. Orienty, F. Fiory, F. Caruso, M. Miele, C. Maitan, M. A. Andreozzi, F. Vigliotta, G. Condorelli, G. Beguinot, F., Insulin-activated protein kinase Cbeta bypasses Ras and stimulates mitogen-activated protein kinase activity and cell proliferation in muscle cells, *Mol Cell Biol.*, 2000, 20, 6323-6333

Freinkel, R. K. Woodley, D. T., The biology of the skin. Publisher: the Parthenon publishing group, 2001, Pearl River, N.Y. USA, ISDN 1850700060

Gartsbein, M. Alt, A. Hashimoto, K. Nakajima, K. Kuroki, T. Tennenbaum, T., The role of protein kinase C delta activation and STAT3 Ser727 phosphorylation in insulin-induced keratinocyte proliferation, *J Cell Sci.*, 2006, 119, 470-481

Gregoire, F. M., Adipocyte differentiation: from fibroblast to endocrine cell, *Exp Biol Med*, 2001, 226, 997-1002

Hofmann, J., The potential for isoenzyme-selective modulation of protein kinase C, *The FASEB J*, 1997, 11, 649-669

Ishiki, M. Klip, A., Minireview: recent developments in the regulation of glucose transporter-4 traffic: new signals, locations, and partners, *Endocrinology*, 2005, 146, 5071-5078

Jackson, S. M. Williams, M. L. Feingold K. R. Elias, P. M., Pathobiology of the stratum corneum, *West J Med.*, 1993, 158, 279-285

Laviola, L. Perrini, S. Cignarelli, A. Giorgino, F., Insulin signalling in human adipose tissue, *Arch Physiol Biochem.*, 2006, 112, 82-88

Maianu, L. Keller, S. R. Garvey, W. T., Adipocytes exhibit abnormal subcellular distribution and translocation of vesicles containing glucose transporter 4 and insulin-regulated aminopeptidase in type 2 diabetes mellitus: implications regarding defects in vesicle trafficking, *J Clin Endocrinol Metab.*, 2001, 86, 5450-5456

Montagna, W. Carlisle, K., Structural changes in aging human skin, *J Invest Dermatol.*, 1979, 73, 47-53

Muller, L. M. Goiter, K. J. HAK, E. Goudzwaard, W. L. Schellevis, F. G. Hoepelman, A. I. Rutten, G. E., Increased risk of common infections in patients with type 1 and type 2 diabetes mellitus, *Clin Infect Dis.*, 2005, 41, 281-288

Nakagami, H. et al., *J Atheroscler. Thromb.*, 2006

Ng, T. Parsons, M. Hughes, W. E. Monypenny, J. Zicha, D. Gautreau, A. Arpin, M. Gschmeissner, S. Verveer, P. J. Bastiaens, P. I. Parker, P. J., Ezrin is a downstream effector of trafficking PKC-integrin complexes involved in the control of cell motility, *EMBO J.*, 2001, 20, 2723-2741

Pantanetti, P. Garrapa, G. G. Mantero, F. Boscaro, M. Faloia, E. Venarucci, D., Adipose tissue as an endocrine organ? A review of recent data related to cardiovascular complications of endocrine dysfunctions, *Clin Exp Hypertens.*, 2004, 26, 387-398

Patel, N. Huang, C. Klip, A., Cellular location of insulin-triggered signals and implications for glucose uptake, *Pflugers Arch.*, 2006, 451, 499-510

Schaefer, H. Redelmeier, T. E., Structure and dynamics of the skin barrier. In: Skin barrier: principles of percutaneous absorption. Basel, Switzerland, Karger, 1996, 1-42

Shen, S. Alt, A. Wertheimer, E. Gartsbein, M. Kuroki, T. Ohba, M. Braiman, L. Sampson, S. R. Tennenbaum, T., PKCdelta activation: a divergence point in the signaling of insulin and IGF-1-induced proliferation of skin keratinocytes, *Diabetes,* 2001, 50, 255-264

Spravchikov, N. Sizyakov, G. Gartsbein, M. Accili, D. Tennenbaum, T. Wertheimer, E., Glucose effects on skin keratinocytes: implications for diabetes skin complications, *Diabetes,* 2000, 50, 1627-1635

Taha, C. Klip, A., The insulin signaling pathway, *J. Membrane Biol.*, 1999, 169, 1-12

Tennenbaum, T. Yuspa, S. H. Knox, B. Sobel, M. E. Castronovo, V. Yamada, Y. De Luca, L. M., Alterations in attachment to laminin and localization of laminin binding proteins during differentiation of primary mouse keratinocytes in vitro (Abstract), *J. Invest. Dermatol.*, 1991, 96

Tingo, X. T. Dimg, S. Y. Hansen, B. C., Paradoxical increase in dermal microvascular flow in pre-diabetes associated with elevated levels of CRP, *Clin Hemorheol Microcirc.*, 2006, 34, 273-282

Varani, J. Dame, M. K. Rittie, L. Fligiel, S. E. Kang, S. Fisher, G. J. Voorhees, J. J., Decreased collagen production in chronologically aged skin: roles of age-dependent alteration in fibroblast function and defective mechanical stimulation, *Am J Pathol.*, 2006, 168, 1861-1868

Wang, Y. R. Margolis, D., The prevalence of diagnosed cutaneous manifestations during ambulatory diabetes visits in the United States, 1998-2002, *Dermatology,* 2006, 212, 229-234

Wertheimer, E. Enk, C. D., Skin and diabetes mellitus, *Diabetes Mellitus: a fundamental and clinical text*, Chapter 96, 2001

Wertheimer, E. Spravchikov, N. Trebicz, M. Gartsbein, M. Accili, D. Avinoah, I. Nofeh-Moses, S. Sizyakov, G. Tennenbaum, T., The regulation of skin proliferation and differentiation in the IR null mouse: implications for skin complications of diabetes, *Endocrinology,* 2001, 142, 1234-1241

Wertheimer, E., Diabetic skin complications: a need for reorganizing the categories of diabetes-associated complications, *Isr. Med. Assoc. J.*, 2004, 6, 287-289

West, M. D., The cellular and molecular biology of skin aging, *Arch Dermatol.*, 1994, 130, 87-95

White, M. F., The insulin signalling system and the IRS proteins, *Diabetologia.*, 1997, 40 Suppl 2, 2-17

Wysocki, A. B., Skin, anatomy, physiology, and pathophysiology, *Nurs. Clin. North Am.*, 1999, 34, 777-797

Yang, S. Litchfield, J. E. Baynes, J. W., AGE-breakers cleave model compounds, but do not break Maillard crosslinks in skin and tail collagen from diabetic rats, *Arch Biochem Biophys.*, 2003, 412, 42-46

Yoon, H. S. Baik, S. H. Oh, C. H., Quantitative measurement of desquamation and skin elasticity in diabetic patients, *Skin Res Technol.*, 2002, 8, 250-254

Yuspa, S. H. Kilkenny, A. E. Steinert, P. M. Roop, D. R., Expression of murine epidermal differentiation markers is tightly regulated by restricted extracellular calcium concentrations in vitro, *J. Cell Biol.*, 1989, 109, 1207-1217

---

The invention claimed is:

1. A method comprising treating a skin pathology, disorder, or condition associated with aging by topically administering to the skin of an individual who is aging, a cosmetically effective amount of at least one agent capable of restoring an impaired physiological condition of the skin associated with said skin pathology, disorder, or condition, wherein said at least one agent is a PKC isoform modulator capable of modulating at least one of the expression or activity of at least one PKC isoform selected from PKCα, PKCβ, PKCδ, PKCε, PKGη, PKCξ, PKCγ, PKCθ, PKCλ, or PKCτ, wherein said at least one agent is a PKC isoform inhibitor, which may be a PKC isoform pseudosubstrate inhibitor, a peptide binding to the PKC isoform substrate region, a peptide binding to the ATP-binding site of a PKC isoform, or Copolymer-1.

2. A method comprising treating a skin pathology, disorder, or condition associated with aging by topically administering to the skin of an individual who is aging, a cosmetically effective amount of at least one agent capable of restoring an impaired physiological condition of the skin associated with said skin pathology, disorder, or condition wherein said at least one agent is a PKCα pseudosubstrate inhibitor selected from the group of peptides consisting of SEQ ID NO: 1 to SEQ ID NO: 7, or a peptide binding to the PKCα substrate region selected from the group of peptides consisting of SEQ ID NO: 8 to SEQ ID NO: 24.

3. A method comprising treating a skin pathology, disorder, or condition associated with aging by topically, administering to the skin of an individual who is aging, a cosmetically effective amount of at least one agent capable of restoring an impaired physiological condition of the skin associated with said skin pathology, disorder, or condition wherein said at least one agent is the N-myristoylated PKCct pseudosubstrate peptide of SEQ ID NO: 1.

4. A method comprising treating a skin pathology, disorder, or condition associated with aging by topically administering to the skin of an individual who is aging, a cosmetically effective amount of at least one agent capable of restoring an impaired physiological condition of the skin associated with said skin pathology, disorder, or condition, wherein said at least one agent is the N-myristoylated PKCα pseudosubstrate peptide of SEQ ID NO: 1 in a concentration ranging from 0.01 μM to 10 μM.

5. A method comprising treating a skin pathology, disorder, or condition associated with is aging, by topically administering to the skin of an individual who is aging, a cosmetically effective amount of at least one agent capable of restoring an impaired physiological condition of the skin associated with said skin pathology, disorder, or condition, wherein said at least one agent is the N-myristoylated PKCα pseudosubstrate peptide of SEQ ID NO: 1 in a concentration ranging from 0.01 μM to 10 μM in combination with insulin in a concentration ranging from 0.01 μM to 10 μM.

6. A method comprising treating a skin pathology, disorder, or condition associated with aging by topically administering to the skin of an individual who is aging, a cosmetically effective amount of at least one agent capable of restoring an impaired physiological condition of the skin associated with said skin pathology, disorder, or condition, wherein said at least one agent is the N-myristoylated PKCα pseudosubstrate peptide of SEQ ID NO: 1 in a concentration ranging from 0.01 μM to 10 μM in combination with insulin in a concentration ranging from 0.01 μM to 10 μM.

7. The method of claim 5, wherein said N-myristoylated PKCα pseudosubstrate peptide of SEQ ID NO: 1 is present in a concentration ranging from 0.01 μM to 10 μM and the insulin in a concentration ranging from 0.01 μM to 10 μM.

8. The method of claim 5, wherein said N-myristoylated PKCα pseudosubstrate peptide of SEQ ID NO: 1 is present in a concentration ranging from 0.01 μM to 10 μM and the insulin is present in a concentration ranging from 0.01-2 μM.

9. The method of claim 5 wherein said N-myristoylated PKCα pseudosubstrate peptide of SEQ ID NO: 1 is present concentration ranging from 0.01 μM to 10 μM and the insulin is present in a concentration of $7\times10^{-8}$ M.

10. The method of claim 6, wherein said N-myristoylated PKCα pseudosubstrate peptide of SEQ ID NO: 1 is present in a concentration ranging from 0.01 μM to 10 μM and the insulin in a concentration ranging from 0.01 μM to 10 μM.

11. The method of claim 6, wherein said N-myristoylated PKCα pseudosubstrate peptide of SEQ ID NO: 1 is present in a concentration ranging from 0.01 μM to 10 μM and the insulin is present in a concentration ranging from 0.01-2 μM.

12. The method of claim 6 wherein said N-myristoylated PKCα pseudosubstrate peptide of SEQ ID NO: 1 is present concentration ranging from 0.01 μM to 10 μM and the insulin is present in a concentration of $7\times10^{-8}$ M.

* * * * *